(12) United States Patent
Gallagher et al.

(10) Patent No.: US 9,464,321 B2
(45) Date of Patent: Oct. 11, 2016

(54) METHODS AND REAGENTS THAT SPECIFICALLY DETECT, DISTINGUISH AND QUANTIFY IFN-λ2 MRNA FROM IFN-λ3 MRNA IN HUMANS

(71) Applicants: Grant Gallagher, Milltown, NJ (US); Grant E. Gallagher, Milltown, NJ (US); Joyce Eskdale, Milltown, NJ (US); Rachael Siegel, Fords, NJ (US)

(72) Inventors: Grant Gallagher, Milltown, NJ (US); Grant E. Gallagher, Milltown, NJ (US); Joyce Eskdale, Milltown, NJ (US); Rachael Siegel, Fords, NJ (US)

(73) Assignee: Medical Diagnostic Laboratories, LLC, Hamilton, NJ (US)

( * ) Notice: Subject to any disclaimer, the term of this patent is extended or adjusted under 35 U.S.C. 154(b) by 127 days.

(21) Appl. No.: 14/215,525

(22) Filed: Mar. 17, 2014

(65) Prior Publication Data

US 2014/0272994 A1    Sep. 18, 2014

Related U.S. Application Data

(60) Provisional application No. 61/791,419, filed on Mar. 15, 2013.

(51) Int. Cl.
*C12P 19/34* (2006.01)
*C12Q 1/68* (2006.01)

(52) U.S. Cl.
CPC ....... *C12Q 1/6876* (2013.01); *C12Q 2600/158* (2013.01)

(58) Field of Classification Search
CPC ............. H04B 1/1027; H04B 1/7102; H04B 2201/709718; H04J 11/0066
USPC ....................................................... 435/91.2
See application file for complete search history.

(56) References Cited

U.S. PATENT DOCUMENTS

| | | | |
|---|---|---|---|
| 2005/0037012 A1* | 2/2005 | Brady | C07K 14/54 424/161.1 |
| 2011/0311973 A1* | 12/2011 | Rabin | C12Q 1/6858 435/6.11 |

OTHER PUBLICATIONS

Levy, David and García-Sastre, Adolfo, The virus battles: IFN induction of the antiviral state and mechanisms of viral evasion, Cytokine & Growth Factor Reviews, 2001, 12 143-156, Elsevier.
Dalton, Dyana, et al, Multiple Defects of Immune Cell Function in Mice with Disrupted Interferon-γ Genes, Science, Mar. 1993, 259 (5102) 1739-1742, American Association for the Advancement of Science.
Dorman, Susan, et al., Clinical features of dominant and recessive interferon γ receptor 1 deficiencies, Lancet, Dec. 2004, 364 (9451) 2113-2121, Elsevier.
Bach, Erika, et al., The IFNγ Receptor: A Paradigm for Cytokine Receptor Signaling, Annual Review of Immunology, 1997, 15 563-591, Annual Reviews.
Kotenko, Sergei, et al., IFN-λs mediate antiviral protection through a distinct class II cytokine receptor complex, Nature Immunology, Dec. 2002, 4(1) 69-77, Nature Publishing Group.
Sheppard, Paul, et al., IL-28, IL-29 and their class II cytokine receptor IL-28R, Nature Immunology, Dec. 2002, 4(1) 63-68, Nature Publishing Group.
Wu, Ligang and Belasco, Joel, Let Me Count the Ways: Mechanisms of Gene Regulation by miRNAs and siRNAs, Molecular Cell Review, Jan. 2008, 29(1) 1-7, Cell Press.
Roch, Florence and Bach, Marie-Anne, Strain Differences in Mouse Cellular Responses to Mycobacterium lepraemurium and BCG Subcutaneous Infection, Clinical and Experimental Immunology, Jun. 1990, 80(3): 332-338. John Wiley & Sons, Inc.
Siegel, Rachael, et al., Regulation of IFN-λ1 promoter activity (IFN-λ1/IL-29) in human airway epithelial cells. The Journal of Immunology, Dec. 2011, 187(11) 5636-5644, The American Association of Immunologists.
Cannella, Fabiana, et al., Interferon lamda 1 expression in cervical cells differs between low-risk and high-risk human papillomavirus-positive women, Medical Microbiology and Immunology, Feb. 2014, DOI 10.1007/s00430-014-0330-9, Springer Publishing.
Wittwer, Carl, et al., Continuous Fluorescence Monitoring of Rapid Cycle DNA Amplification, BioTechniques, Jan. 1997, 22:130-138, Informa BioSciences.

* cited by examiner

*Primary Examiner* — Cynthia B Wilder
(74) *Attorney, Agent, or Firm* — Siu K. Lo

(57) ABSTRACT

The present invention provides a method of specifically detecting IFN-λ2 mRNA or IFN-λ3 mRNA. There is provided a qRT-PCR method specifically detecting, discriminating and quantifying IFN-λ2 and IFN-λ3 mRNA in a biological sample obtained from a human. There is provided qRT-PCR methods and primers and probes that specifically detect IFN-λ2 mRNA but not IFN-λ3 mRNA and vice versa in humans in order to detect, quantify and discriminate IFN-λ2 mRNA and IFN-λ3 mRNA.

12 Claims, 26 Drawing Sheets

λ2  241 CTTAGAAGAGTCGCTTCTTGCTGAAGGACTGC...TTGCCATTCCGCTTCTTCCCAGGAC 300
λ3  181 CTTAGAAGAGTCGCTTCTTGCTGAAGGACTGC...TTGCCGTTCCGCTTCTTCCCAGGAC 240
                                          262 ←— SEQ ID NO: 3 —→ 279

λ2  301 CTGGGGACCTGAGCCAGCCTGCAGGTTGAGGCCCC...ATCGCTTTGGAGGCTGACCTGGC 360
λ3  241 CTGGGGACCTGAGCCAGCCTGCAGGTTGAGGCCCC...ATCGCGTTTGGAGGCTGACCTGGC 300
                              338 ←— SEQ ID NO: 4 —→ 355

(241-360 of SEQ ID NO: 15)
(181-300 of SEQ ID NO: 16)

Figure 3

λ2 Synthetic Oligo (SEQ ID NO: 1)

```
                            SEQ ID NO: 3
                    ──────────────────────────────────────▶
242  TTA GAA GAG TCG CTT CTG AAG GAC TGC A GG  TGC CAG  280
281  TCC CGC CTC TTC CCC AGG ACC TGG GAC CTG AGG CAG  319
                                  SEQ ID NO: 4
                             ◀────────────────────────────
320  CAG GTG AGG GAG CGC CCC A TG  GCT TTG GAG GCT GAG  358
359  GCC CTG ACG CTG AAG GTC TGG AGG CCA CCG CTG       391
```

λ3 Synthetic Oligo (SEQ ID NO: 2)

```
                            SEQ ID NO: 3
                    ──────────────────────────────────────▶
182  TTA GAA GAG TCG CTT CTG AAG GAC TGC A AG  TGC C GC   220
221  TCC CGC CTC TTC CCC AGG ACC TGG GAC CTG AGG CAG  259
                                  SEQ ID NO: 4
                             ◀────────────────────────────
260  CAG GTG AGG GAG CGC CCC G TG  GCT TTG GAG GCT GAG  298
299  GCC CTG ACG CTG AAG GTC TGG AGG CCA CCG CTG       337
```

Figure 9

Sequencing of Dendritic cell Amplicon

```
Score =  174 bits (94),  Expect = 2e-48
Identities = 94/94 (100%),  Gaps = 0/94 (0%)
Strand=Plus/Plus
```

```
262  GAAGGACTGCAGGTGCCACTCCCGGCTCTTCCCAGGACCTGGTGACCTGGAGGCAGCTGCA  321
     ||||||||||||||||||||||||||||||||||||||||||||||||||||||||||||
1    GAAGGACTGCAGGTGCCACTCCCGGCTCTTCCCAGGACCTGGTGACCTGGAGGCAGCTGCA  60

322  GGTCGAGGGAGCCGCCCATGGCTTTGGAGGCTCAG  355     mRNA λ2 (262-355 of SEQ ID NO: 15)
     |||||||||||||||||||||||||||||||||||
61   GGTCGAGGGAGCCGCCCATGGCTTTGGAGGCTCAG  94      λ2 Amplicon SEQ ID NO: XX
```

λ2  361 CCTTGACGGCAGAGGTTCTGGAGGCCACCCTGACCGCCCTGGGTCTT 420
λ3  301 CCTTGACGGCAGAGGTTCTGGAGGCCACCCTGACCGCCCTGGGTCTT 360
                                        339 →←SEQ ID NO: 10→ 355

λ2  421 GGACCAGCCCTTCACACCTGCACACCATATCCTTCCCAGGCCTGTATCCAGCC 480
λ3  361 GGACCAGCCCTTCACACCTGCACACCATATCCTTCCCAGGCCTGTATCCAGCC 420
                                        401 →←SEQ ID NO: 11→ 419

Figure 13

λ2 Synthetic oligo (SEQ ID NO: 6)

```
364 GAC GCT GAA GGT TCT GGA GGC CAC CGC TGA CAC CCC 402
        SEQ ID NO: 10
403 AGC CCT GGT GGA CTT GGA CCA GCC CCT TCA CAC CCT 441
                                 SEQ ID NO: 11
442 GCA CCA TAT CCT CTC CCA GTT CCG GGC CTG TAT CCA GCC 480
481 TCA GCC CAC GGC AGG GCC CAG GAC CCG GGG CCG 513
```

λ3 Synthetic oligo (SEQ ID NO: 7)

```
304 GAC GCT GAA GGT TCT GGA GGC CAC CGC TGA CAC CCC 342
        SEQ ID NO: 10
343 AGC CCT GGT GGA CTT GGA CCA GCC CCT TCA CAC CCT 381
                                 SEQ ID NO: 11
382 GCA CCA TAT CCT CTC CCA GCT CCG GGC CTG TAT CCA GCC 420
421 TCA GCC CAC GGC AGG GCC CAG GAC CCG GGG CCG 453
```

Figure 20

Sequencing of Dendritic Cell Amplicon

```
Score =  150 bits (81),  Expect = 2e-41
Identities = 81/81 (100%), Gaps = 0/81 (0%)
Strand=Plus/Plus 339  ACCCAGCCCTGCGGGATGTCTTGGACCAGCCAGCCCTTCACACCCTGCACCATATCCTCCC  398
     |||||||||||||||||||||||||||||||||||||||||||||||||||||||||||||
1    ACCCAGCCCTGCGGGATGTCTTGGACCAGCCAGCCCTTCACACCCTGCACCATATCCTCCC  60

399  AGCTCCGGGCCTGTATCCAGC  419    mRNA λ3 (SEQ ID NO: 16)
     |||||||||||||||||||||
61   AGCTCCGGGCCTGTATCCAGC  81     λ3 Amplicon (SEQ ID NO: XX)
```

Figure 21

λ2  361 CCTGACGCTTGAAGGTTCTGGAGGCCTGACACTGACTGACCGCCACCGGCCAGCCCTG[T]GC[T]CTT 420
λ3  301 CCTGACGCTTGAAGGTTCTGGAGGCCTGACACTGACTGACCGCCACCGGCCAGCCCTG[A]GC[A]CTT 360

339 →  SEQ ID NO: 10  → 355
                                                                337 -- SEQ ID NO: 14  -→ 355

λ2  421 GGACCAGCCGGACCCCCTTCACAACCCTGCACCATATCCTCTCCCA[T]TCCGGGCCTGTATCCAGCC 480
λ3  361 GGACCAGCCGGACCCCCTTCACAACCCTGCACCATATCCTCTCCCA[C]TCCGGGCCTGTATCCAGCC 420

401 ← SEQ ID NO: 11 → 419      (361-480 of SEQ ID NO: 15)
                                                      401 ←- SEQ ID NO: 11 -→ 419    (301-420 of SEQ ID NO: 16)

Figure 22

SEQUENCE LISTING

```
<160> NUMBER OF SEQ ID NOS: 20

<210> SEQ ID NO 1
<211> LENGTH: 150
<212> TYPE: DNA
<213> ORGANISM: Artificial Sequence
<220> FEATURE:
<223> OTHER INFORMATION: Oligonucleotide

<400> SEQUENCE: 1
ttagaagagt cgcttctgct gaaggactgc aggtgccact cccgcctctt ccccaggacc        60
tgggacctga ggcagctgca ggtgagggag cgccccatgg ctttggaggc tgagctggcc       120
ctgacgctga aggtctggag gccaccgctg                                         150

<210> SEQ ID NO 2
<211> LENGTH: 150
<212> TYPE: DNA
<213> ORGANISM: Artificial Sequence
<220> FEATURE:
<223> OTHER INFORMATION: Oligonucleotide

<400> SEQUENCE: 2
ttagaagagt cgcttctgct gaaggactgc aagtgccgct cccgcctctt ccccaggacc        60
```

```
tgggacctga ggcagctgca ggtgagggag cgccccgtgg ctttggaggc tgagctggcc      120
ctgacgctga aggtctggag gccaccgctg                                       150

<210> SEQ ID NO 3
<211> LENGTH: 18
<212> TYPE: DNA
<213> ORGANISM: Artificial Sequence
<220> FEATURE:
<223> OTHER INFORMATION: Oligonucleotide Primer

<400> SEQUENCE: 3
gaaggactgc aggtgcca                                                     18

<210> SEQ ID NO 4
<211> LENGTH: 18
<212> TYPE: DNA
<213> ORGANISM: Artificial Sequence
<220> FEATURE:
<223> OTHER INFORMATION: Oligonucleotide Primer

<400> SEQUENCE: 4
ctcagcctcc aaagccat                                                     18

<210> SEQ ID NO 5
<211> LENGTH: 19
<212> TYPE: DNA
<213> ORGANISM: Artificial Sequence
<220> FEATURE:
<223> OTHER INFORMATION: Oligonucleotide Primer

<400> SEQUENCE: 5
gctcagcctc caaagccat                                                    19

<210> SEQ ID NO 6
<211> LENGTH: 150
<212> TYPE: DNA
<213> ORGANISM: Artificial Sequence
<220> FEATURE:
<223> OTHER INFORMATION: Oligonucleotide Primer

<400> SEQUENCE: 6
gacgctgaag gttctggagg ccaccgctga cactgaccca gccctggtgg acgtcttgga       60 ccagccccctt cacaccctgc accatatcct ctcccagttc cgggcctgta tccagcctca    120
gcccacggca gggcccagga cccggggccg                                       150

<210> SEQ ID NO 7
<211> LENGTH: 150
<212> TYPE: DNA
<213> ORGANISM: Artificial Sequence
<220> FEATURE:
<223> OTHER INFORMATION: Oligonucleotide

<400> SEQUENCE: 7
gacgctgaag gttctggagg ccaccgctga cactgaccca gccctgggg atgtcttgga        60 ccagccccctt cacaccctgc accatatcct ctcccagctc cgggcctgta tccagcctca    120
gcccacggca gggcccagga cccggggccg                                       150

<210> SEQ ID NO 8
<211> LENGTH: 19
<212> TYPE: DNA
<213> ORGANISM: Artificial Sequence
<220> FEATURE:
```

```
<223> OTHER INFORMATION: Oligonucleotide

<400> SEQUENCE: 8
tgacccagcc ctggtggac                                                19

<210> SEQ ID NO 9
<211> LENGTH: 19
<212> TYPE: DNA
<213> ORGANISM: Artificial Sequence
<220> FEATURE:
<223> OTHER INFORMATION: Oligonucleotide

<400> SEQUENCE: 9
gctggataca ggcccggaa                                                19

<210> SEQ ID NO 10
<211> LENGTH: 17
<212> TYPE: DNA
<213> ORGANISM: Artificial Sequence
<220> FEATURE:
<223> OTHER INFORMATION: Oligonucleotide Primer

<400> SEQUENCE: 10
acccagccct gggggat                                                  17

<210> SEQ ID NO 11
<211> LENGTH: 19
<212> TYPE: DNA
<213> ORGANISM: Artificial Sequence
<220> FEATURE:
<223> OTHER INFORMATION: Oligonucleotide Primer

<400> SEQUENCE: 11
gctggataca ggcccggag                                                19

<210> SEQ ID NO 12
<211> LENGTH: 18
<212> TYPE: DNA
<213> ORGANISM: Artificial Sequence
<220> FEATURE:
<223> OTHER INFORMATION: Oligonucleotide Primer

<400> SEQUENCE: 12
gaaggactgc aagtgccg                                                 18

<210> SEQ ID NO 13
<211> LENGTH: 18
<212> TYPE: DNA
<213> ORGANISM: Artificial Sequence
<220> FEATURE:
<223> OTHER INFORMATION: Oligonucleotide Primer

<400> SEQUENCE: 13
ctcagcctcc aaagccac                                                 18

<210> SEQ ID NO 14
<211> LENGTH: 19
<212> TYPE: DNA
<213> ORGANISM: Artificial Sequence
<220> FEATURE:
<223> OTHER INFORMATION: Oligonucleotide Primer

<400> SEQUENCE: 14
tgacccagcc ctgggggat                                                19
```

```
<210> SEQ ID NO 15
<211> LENGTH: 734
<212> TYPE: DNA
<213> ORGANISM: Homo sapiens
<220> FEATURE:
<221> NAME/KEY: mRNA
<222> LOCATION: (1)..(595)

<400> SEQUENCE: 15
tgggtgacag cctcagagtg tttcttctgc tgacaaagac cagagatcag gaatgaaact      60
agacatgact ggggactgca cgccagtgct ggtgctgatg ccgcagtgc tgaccgtgac     120 tggagcagtt cctgtcgcca ggctccacgg ggctctcccg gatgcaaggg gctgccacat    180
agcccagttc aagtccctgt ctccacagga gctgcaggcc tttaagaggg ccaaagatgc    240
cttagaagag tcgcttctgc tgaaggactg caggtgccac tcccgcctct tcccaggac    300 ctgggacctg aggcagctgc aggtgaggga gcgcccatg gctttggagg ctgagctggc    360
cctgacgctg aaggttctgg aggccaccgc tgacactgac ccagccctgg tggacgtctt   420
ggaccagccc cttcacaccc tgcaccatat cctctcccag ttccgggcct gtatccagcc   480
tcagcccacg gcagggccca ggacccgggg ccgcctccac cattggctgt accggctcca   540
ggaggcccca aaaaggagt cccctggctg cctcgaggcc tctgtcacct tcaacctctt    600
ccgcctcctc acgcgagacc tgaattgtgt tgccagtggg gacctgtgtg tctgaccctc   660
ccaccagtca tgcaacctga gatttattt ataaattagc cacttgtctt aatttattgc    720
cacccagtcg ctat                                                     734

<210> SEQ ID NO 16
<211> LENGTH: 595
<212> TYPE: DNA
<213> ORGANISM: Homo sapiens
<220> FEATURE:
<221> NAME/KEY: mRNA
<222> LOCATION: (1)..(595)

<400> SEQUENCE: 16
agacatgacc ggggactgca tgccagtgct ggtgctgatg ccgcagtgc tgaccgtgac      60 tggagcagtt cctgtcgcca ggctccgcgg ggctctcccg gatgcaaggg gctgccacat    120
agcccagttc aagtccctgt ctccacagga gctgcaggcc tttaagaggg ccaaagatgc    180
cttagaagag tcgcttctgc tgaaggactg caagtgccgc tcccgcctct tcccaggac    240 ctgggacctg aggcagctgc aggtgaggga gcgccccgtg gctttggagg ctgagctggc    300
cctgacgctg aaggttctgg aggccaccgc tgacactgac ccagccctgg gggatgtctt   360
ggaccagccc cttcacaccc tgcaccatat cctctcccag ctccgggcct gtatccagcc   420
tcagcccacg gcagggccca ggacccgggg ccgcctccac cattggctgc accggctcca   480
ggaggcccca aaaaggagt cccctggctg cctcgaggcc tctgtcacct tcaacctctt    540
ccgcctcctc acgcgagacc tgaattgtgt tgccagcggg gacctgtgtg tctga        595

<210> SEQ ID NO 17
<211> LENGTH: 20
<212> TYPE: DNA
<213> ORGANISM: Artificial Sequence
<220> FEATURE:
<223> OTHER INFORMATION: Oligonucleotide Primer

<400> SEQUENCE: 17
tttaagaggg ccaaagatgc                                                20
```

```
<210> SEQ ID NO 18
<211> LENGTH: 20
<212> TYPE: DNA
<213> ORGANISM: Artificial Sequence
<220> FEATURE:
<223> OTHER INFORMATION: Oligonucleotide Primer

<400> SEQUENCE: 18
tgggctgagg ctggatacag                                              20

<210> SEQ ID NO 19
<211> LENGTH: 61
<212> TYPE: DNA
<213> ORGANISM: Homo sapiens

<400> SEQUENCE: 19
gaaggactgc aggtgccact cccgcctctt ccccaggacc tgggacctga ggcagctgca  60
g                                                                  61

<210> SEQ ID NO 20
<211> LENGTH: 81
<212> TYPE: DNA
<213> ORGANISM: Homo sapiens

<400> SEQUENCE: 20
acccagccct gggggatgtc ttggaccagc cccttcacac cctgcaccat atcctctccc  60
agctccgggc ctgtatccag c                                            81
```

METHODS AND REAGENTS THAT SPECIFICALLY DETECT, DISTINGUISH AND QUANTIFY IFN-λ2 MRNA FROM IFN-λ3 MRNA IN HUMANS

CROSS-REFERENCE TO RELATED APPLICATION

This application claims the benefit under 35 U.S.C. §119 (e) to U.S. Provisional Application No. 61/791,419 filed Mar. 15, 2013, the content of which is incorporated by reference herein in its entirety.

FIELD OF THE INVENTION

The present invention relates to PCR methods specifically identifying and discriminating the presence of IFN-λ2 and IFN-λ3 in a sample. Specifically, the present invention provides methods and primers and probes for the quantitative RT-PCR methods that specifically detect and distinguish IFN-λ2 mRNA from IFN-λ3 mRNA in humans.

BACKGROUND OF THE INVENTION

Interferons (IFNs) are key cytokines in the establishment of a multifaceted antiviral response. Based on the structural features, receptor usage and biological activities, there are (3) distinct types of IFNs, commonly recognized as type I, II, and III IFNs.

Although IFNs are important mediators of antiviral protection, their roles in antiviral defense vary. For example, type I IFNs (IFN-α/β/ω/εκ in humans) possess strong intrinsic antiviral activity, and are able to induce a potent antiviral state in a wide variety of cells (Levy and Garcia-Sastre 2001). In contrast, studies with IFN-γ and IFN-γ receptor knock-out mice (Dalton et al., 1993) as well as analysis of humans who possess inherited genetic mutations of the IFN-γ receptor (Dorman et al., 2004) reveal that antiviral activity is not the primary biological function of IFN-γ. IFN-γ is classified as a Th1-type cytokine that stimulates cell-mediated immune responses that are critical for the development of host protection against pathogenic intracellular microorganisms such as *Mycobacterium tuberculosis* (Bach et al., 1997) as well as antitumor immune responses.

The most recent additions are the type III IFNs (IFN-λs). They demonstrate structural features of the IL-10-related cytokines but also induce antiviral activity in a variety of target cells, which supports their functional classification as a new type of IFNs (Kotenko et al., 2003). The Interferon-λ (IFN-λ) family was reported in early 2003 (Kotenko et al., 2003; Sheppard et al., 2003). Three (3) IFN-λ genes were identified as encoding three (3) distinct, albeit highly-related, proteins denoted as IFN-λ1, IFN-λ2, and IFN-λ3, respectively. Together, they comprise the type III subset of interferons (IFNs)—distinct from both type I and type II IFNs. Phylogenetically, the IFN-λ genes reside somewhere between the type I IFN and IL-10 gene families. Amino acid sequence comparisons show that the type III IFNs exhibit about ~5%-18% identity with either type I IFNs or the IL-10-related cytokines.

Direct detection techniques for IFN-λ2 or IFN-λ3 mRNA include PCR techniques involving a design of primers and probe-based hybridization. However, the mRNA sequences of IFN-λ2 and IFN-λ3 in human exhibit a 98% identity. Given such a high degree of identity, it is commonly known to be difficult to distinguish these two (2) mRNAs by routine molecular assays such as qRT-PCR. Put simply, it is difficult to identify unique primer pairs that are specific for IFN-λ2 mRNA but not IFN-λ3 mRNA, and vice-versa. To the best of the inventors' knowledge, there is no PCR techniques that can identify and distinguish human IFN-λ2 or IFN-λ3 mRNAs.

There is a continuing need to develop a molecular diagnostic assay that can specifically detect human IFN-λ2 mRNA but not IFN-λ3 mRNA or vice versa.

SUMMARY OF THE INVENTION

In one aspect, the present invention provides a method of quantifying IFN-λ2 mRNA but not IFN-λ3 mRNA in a biological sample in humans, comprising the steps of: (a) obtaining a biological sample from a human, said biological sample is suspected of having IFN-λ2 mRNA; (b) isolating mRNA from said biological sample; (c) performing a reverse transcription reaction to convert said mRNA to cDNA; (d) performing a qRT-PCR on said cDNA using an IFN-λ2-specific primer set to yield an amplification product, said IFN-λ2 specific primer set containing a forward primer and a reverse primer, wherein said forward primer consisting of SEQ ID NO: 3, and said reverse primer consisting of SEQ ID NO: 4, wherein said IFN-λ2-specific primer set amplifies under conditions suitable for amplification of nucleic acid sequence of IFN-λ2 mRNA and not IFN-λ3 mRNA; and (e) quantifying the amplification product to determine the expression level for the IFN-λ2 mRNA. In a preferred embodiment, the qRT-PCR step is performed using an annealing temperature of 60° C.

In another aspect, the present invention provides a method of quantifying IFN-λ3 mRNA but not IFN-λ2 mRNA in a biological sample in humans, comprising the steps of: (a) obtaining a biological sample from a human, said biological sample is suspected of having IFN-λ3 mRNA; (b) isolating mRNA from said biological sample; (c) performing a reverse transcription reaction to convert said mRNA to cDNA; (d) performing a qRT-PCR on said cDNA using an IFN-λ3-specific primer set, said IFN-λ3 specific primer set containing a forward primer and a reverse primer, wherein said forward primer consisting of SEQ ID NO: 10, and said reverse primer consisting of SEQ ID NO: 11 to yield an amplification product, wherein said IFN-λ3-specific primer set amplifies under conditions suitable for amplification of nucleic acid sequence of IFN-λ3 mRNA and not IFN-λ2 mRNA; and (e) quantifying the amplification product to determine the expression level for the IFN-λ3 mRNA. In a preferred embodiment, the qRT-PCR step is performed using an annealing temperature of 60° C.

The biological sample is suspected to contain IFN-λ3 mRNA. Preferably, the biological sample is a cell or tissue (containing a mixture of cells) obtained from a human. Preferably, the biological sample is a white blood cell, dendritic cell, airway epithelial cell, colon cell, or liver cell.

In another aspect, the present invention provides a method of detecting IFN-λ2 mRNA but not IFN-λ3 mRNA in a biological sample in humans, comprising the steps of: (a) obtaining a biological sample from a human, said biological sample is suspected of having IFN-λ2 mRNA; (b) isolating mRNA from said biological sample; (c) performing a reverse transcription reaction to convert said mRNA to cDNA; (d) performing a qRT-PCR on said cDNA using an IFN-λ2-specific primer set, said IFN-λ2 specific primer set containing a forward primer and a reverse primer, wherein said forward primer consisting of SEQ ID NO: 3, and said reverse primer consisting of SEQ ID NO: 4 to yield an amplification product, wherein said IFN-λ2-specific primer set amplifies under conditions suitable for amplification of nucleic acid sequence of IFN-λ2 mRNA and not IFN-λ3 mRNA; and (e) detecting the amplification product to determine the presence for the IFN-λ2 mRNA, wherein the presence of said amplification product is evidence for the presence of IFN-λ2 mRNA in said biological sample. Preferably, the present invention provides a highly sensitive assay to detect and quantify IFN-λ2 mRNA but not IFN-λ3 mRNA in a biological sample in humans.

In another aspect, the present invention provides a method of detecting IFN-λ3 mRNA but not IFN-λ2 mRNA in a biological sample in humans, comprising the steps of: (a) obtaining a biological sample from a human, said biological sample is suspected of having IFN-λ3 mRNA; (b) isolating mRNA from said biological sample; (c) performing a reverse transcription reaction to convert said mRNA to cDNA; (d) performing a qRT-PCR on said cDNA using an IFN-λ3-specific primer set, said IFN-λ3 specific primer set containing a forward primer and a reverse primer, wherein said forward primer consisting of SEQ ID NO: 10 and said reverse primer consisting of SEQ ID NO: 11 to yield an amplification product, wherein said IFN-λ3-specific primer set amplifies under conditions suitable for amplification of nucleic acid sequence of IFN-λ3 mRNA and not IFN-λ2 mRNA; and (e) detecting the amplification product for the presence of IFN-λ3 mRNA, wherein the presence of said amplification product is evidence for the presence of IFN-λ3 mRNA in said biological sample. Preferably, the present invention provides a highly sensitive assay to detect and quantify IFN-λ3 mRNA but not IFN-λ2 mRNA in a biological sample in humans.

In another aspect, the present invention provides a kit for detecting or quantifying IFN-λ2 mRNA, but not IFN-λ3 mRNA in a biological sample in humans, comprising: (a) a primer set specific for IFN-λ2 mRNA, used in an qRT-PCR reaction, to detect mRNA expression level of IFN-λ2 mRNA; and (b) an instruction for use of a forward primer and a reverse primer to detect said mRNA expression level of said IFN-λ2 mRNA in said biological sample.

In yet another aspect, the present invention provides a kit for detecting or quantifying IFN-λ3 mRNA, but not IFN-λ2 mRNA in a biological sample in humans, comprising: (a) a primer set specific for IFN-λ3 mRNA, used in an qRT-PCR reaction, to detect mRNA expression level of IFN-λ3 mRNA; and (b) an instruction for use of a forward primer and a reverse primer to detect said mRNA expression level of said IFN-λ3 mRNA in said biological sample.

BRIEF DESCRIPTION OF THE DRAWINGS

FIG. 1 depicts the mRNA sequences of IFN-λ2 (SEQ ID NO: 15) and IFN-λ3 (SEQ ID NO: 16). Note that the sequences share 98% identity (or identities) and differ only by 11 nucleic acids, which are indicated by rectangular boxes. Both the start (ATG) and stop (TGA) codons are underlined.

FIG. 2 depicts the binding regions of IFN-λ2-specific primer set in relation to the relevant portions of the mRNA sequences of IFN-λ2 (i.e., 241-360 of SEQ ID NO: 15) and IFN-λ3 (i.e., 181-300 of SEQ ID NO: 16). Primer binding regions are shown with an arrow and the base pair on which they start and end. Forward primer sequence 5'-GAAGGACTGCAGGTGCCA-3' (SEQ ID NO: 3), right arrow; reverse primer sequence 5'-CTCAGCCTC-CAAAGCCAT-3' (SEQ ID NO: 4), left arrow. The three non-homologous base pairs in this region are highlighted (i.e., rectangular boxes).

FIG. 3 depicts the sequence of the synthetic oligonucleotides (oligo) used to optimize the IFN-λ2 primers. The oligo for IFN-λ2 (SEQ ID NO: 1) exactly matches the IFN-λ2 mRNA from bases 242-391 and the oligo for IFN-λ3 (SEQ ID NO: 2) exactly matches the IFN-λ3 mRNA from bases 182-337. Primer binding sites are denoted with an arrow (SEQ ID NOs: 3 and 4) and the non-homologous bases are highlighted (i.e., rectangular boxes).

FIG. 9 depicts the sequence identity of the dendritic cell-derived IFN-λ2 amplicon (SEQ ID NO:19) to that of the NCBI-deposited IFN-λ2 mRNA sequence (corresponds to the 262-355 of SEQ ID NO: 15). Analysis showed a 100% match between the dendritic cell amplicon and the deposited IFN-λ2 mRNA sequence.

FIG. 10 depicts the binding region of an alternate set of IFN-λ2-specific primers (Set 3), which bind in the related region as the final working primers (Set 2). Primer Set 3 shares an identical forward primer as Set 2 (i.e., SEQ ID NO: 3), but a reverse primer having one extra base on the 5' end (5'-GCTCAGCCTCCAAAGCCAT-3') (i.e., SEQ ID NO: 5)

as compared to that of Set 2 (i.e., SEQ ID NO: 4). Note that the addition of this extra base completely ablated the utility of the qRT-PCR and produced no amplification of IFN-λ2.

Figure 10:
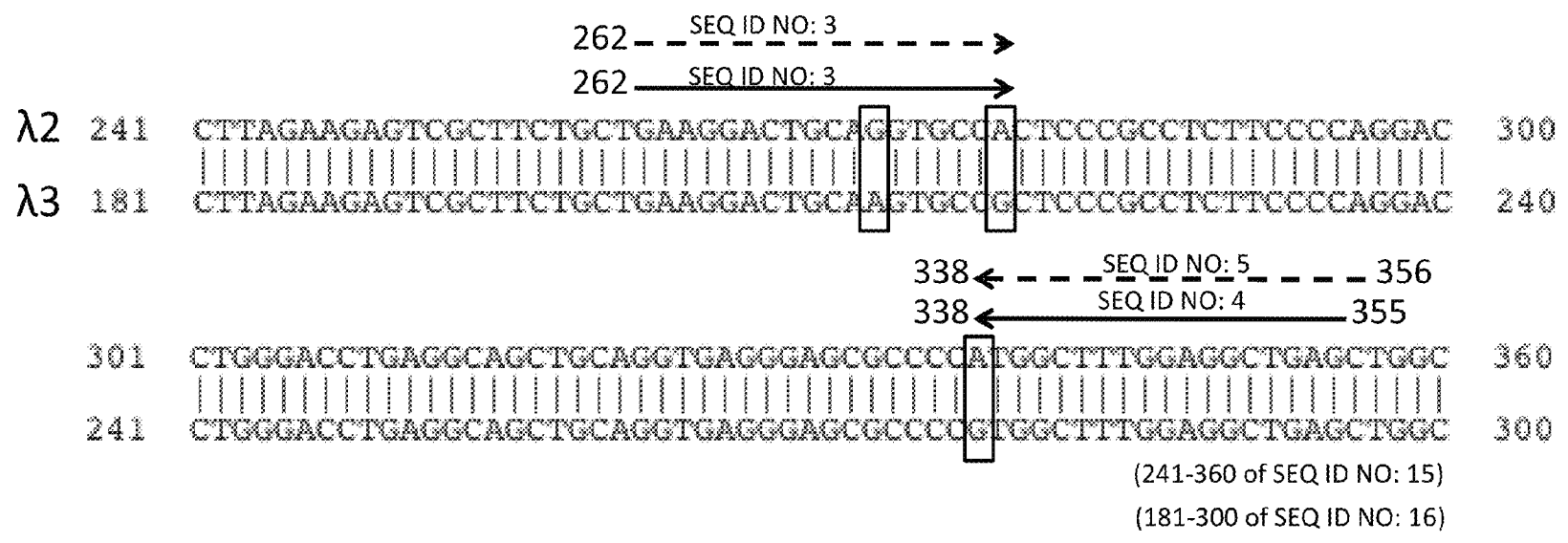
Figure 11:
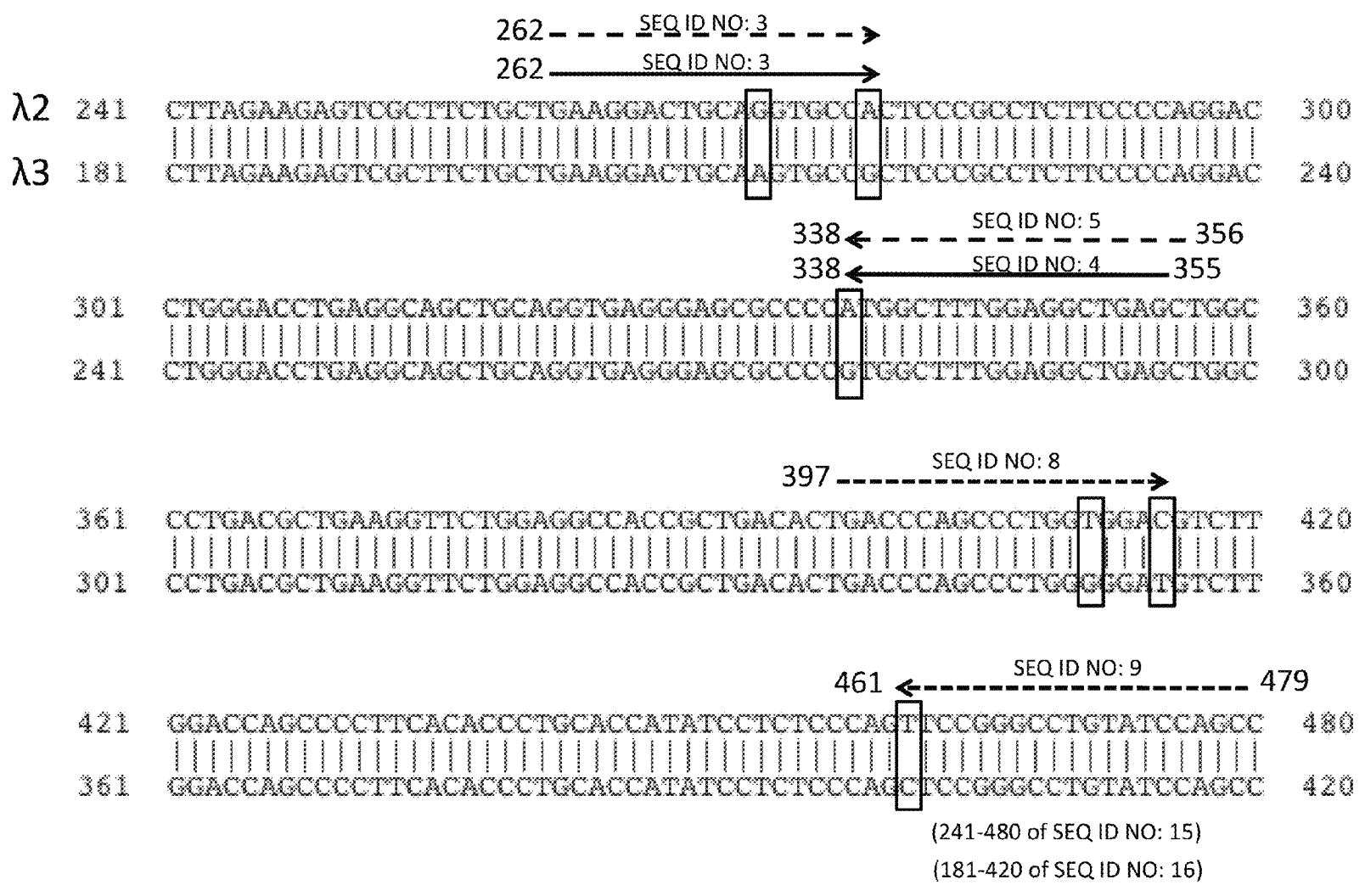

FIG. 11 depicts the binding region of an alternate set of IFN-λ2-specific primers (Set 1). Primer Set 1 spans non-homologous bases that are distinct from that of primer Set 2 (See, FIG. 10; SEQ ID NOS: 3 and 4). Primer Set 1 binds bases 397-415 (forward primer; SEQ ID NO: 8) and 461-479 (reverse primer; SEQ ID NO: 9) produced amplification but also strong primer dimers. Forward primer sequence (SEQ ID NO: 8) is 5'-TGACCCAGCCCTGGTGGAC-3'; reverse primer sequence (SEQ ID NO: 9) is 5'-GCTGGATACAGGCCCGGAA-3'.

FIG. 12 depicts the binding regions of IFN-λ3-specific primer set. Primer binding regions are shown with an arrow and the base pair on which they start and end. Forward primer sequence 5'-ACCCAGCCCTGGGGGAT-3' (SEQ ID NO: 10), right arrow; reverse primer sequence 5'-GCTGGATACAGGCCCGGAG-3' (SEQ ID NO: 11), left arrow. The three non-homologous base pairs in this region are highlighted (i.e., rectangular boxes).

FIG. 13 depicts the sequence of the synthetic oligo used to optimize the IFN-λ3 primers. The oligo for IFN-λ2 (SEQ ID NO: 6) exactly matches the IFN-λ2 mRNA from bases 364-513 and the oligo for IFN-λ3 (SEQ ID NO: 7) exactly matches the IFN-λ3 mRNA from bases 304-453. Primer binding sites are denoted with an arrow (forward primer; SEQ ID NO: 10 and reverse primer; SEQ ID NO: 11) and the non-homologous bases are highlighted (i.e., rectangular boxes).

Figure 14:
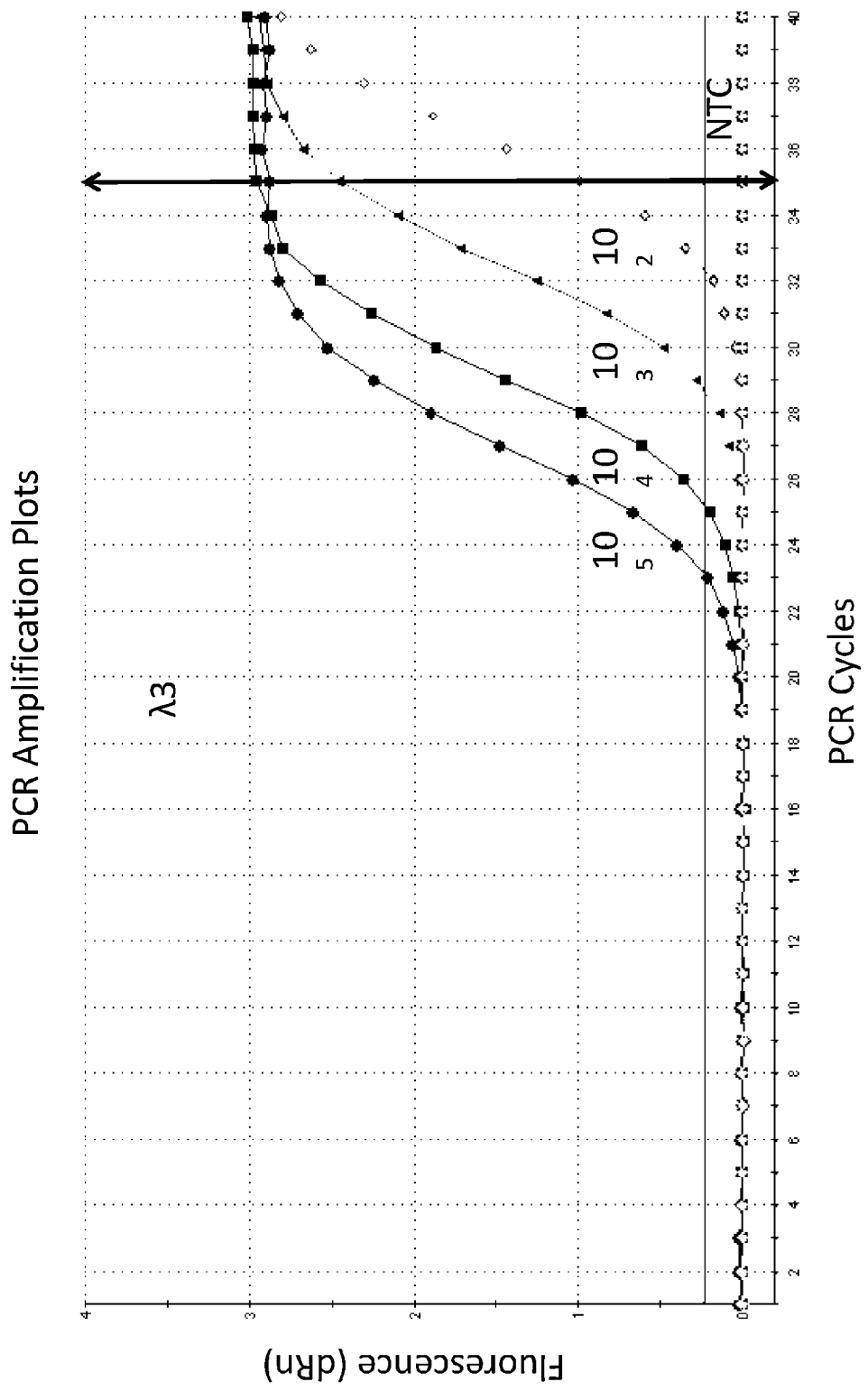

FIG. 14 depicts the sensitivity of the IFN-λ3 qRT-PCR. The figure depicts amplification plots of the IFN-λ3-specific qRT-PCR, using the ten-fold dilutions of the IFN-λ3 synthetic oligo (SEQ ID NO: 7) as a template. The resultant amplification plots demonstrate dose dependent amplification, down to 100 copies of template. No amplification of the template control (NTC) was detected. Fluorescence is displayed as the change in the normalized reporter signal (dRn).

Figure 15:
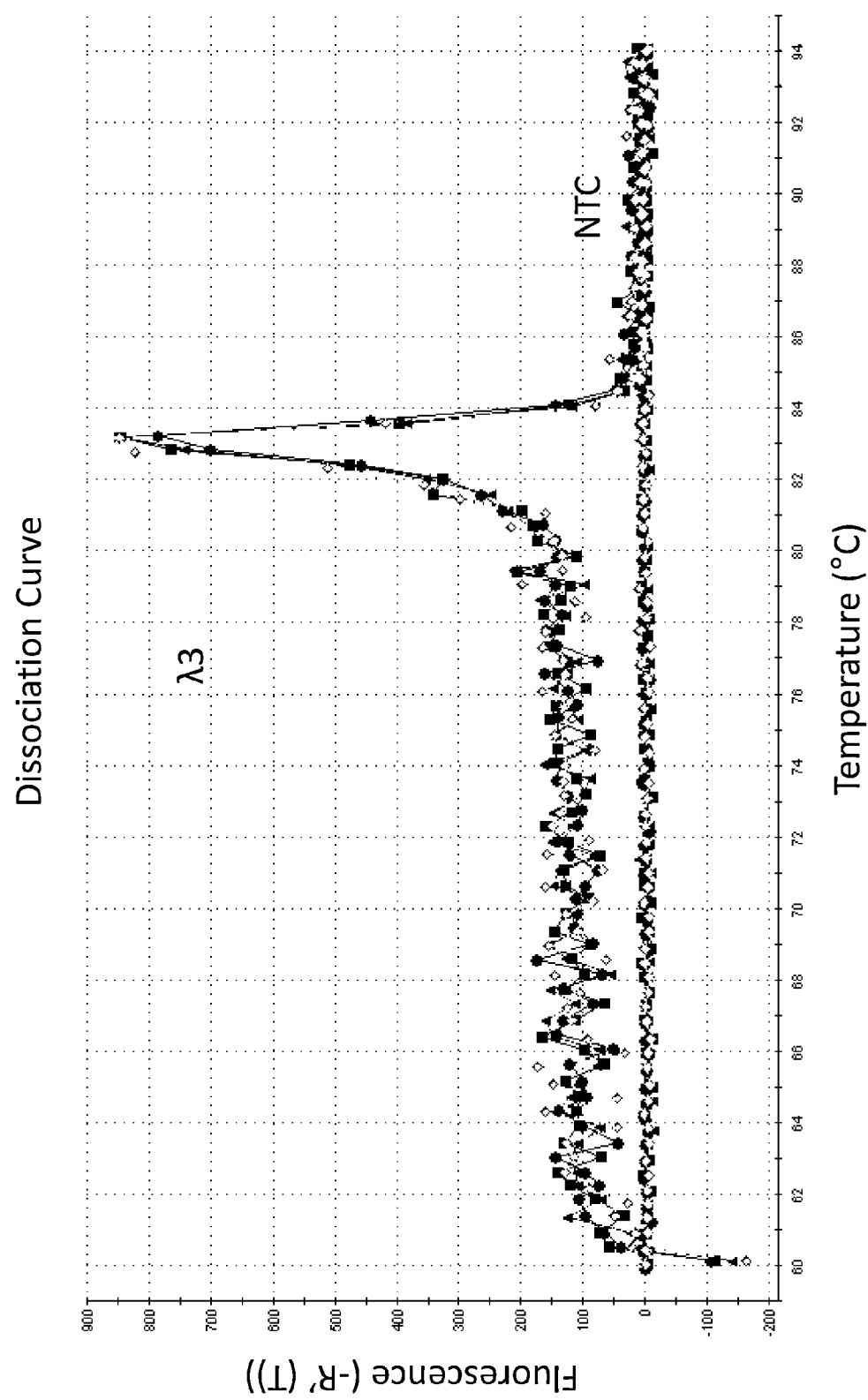

FIG. 15 depicts the dissociation curve (or melting curve) of the single amplicon produced from the IFN-λ3 oligo (SEQ ID NO: 7). The melting temperature is shown to be 83° C. Fluorescence is shown as the negative of the decrease in fluorescence as a function of temperature (−R'(T)).

Figure 16:
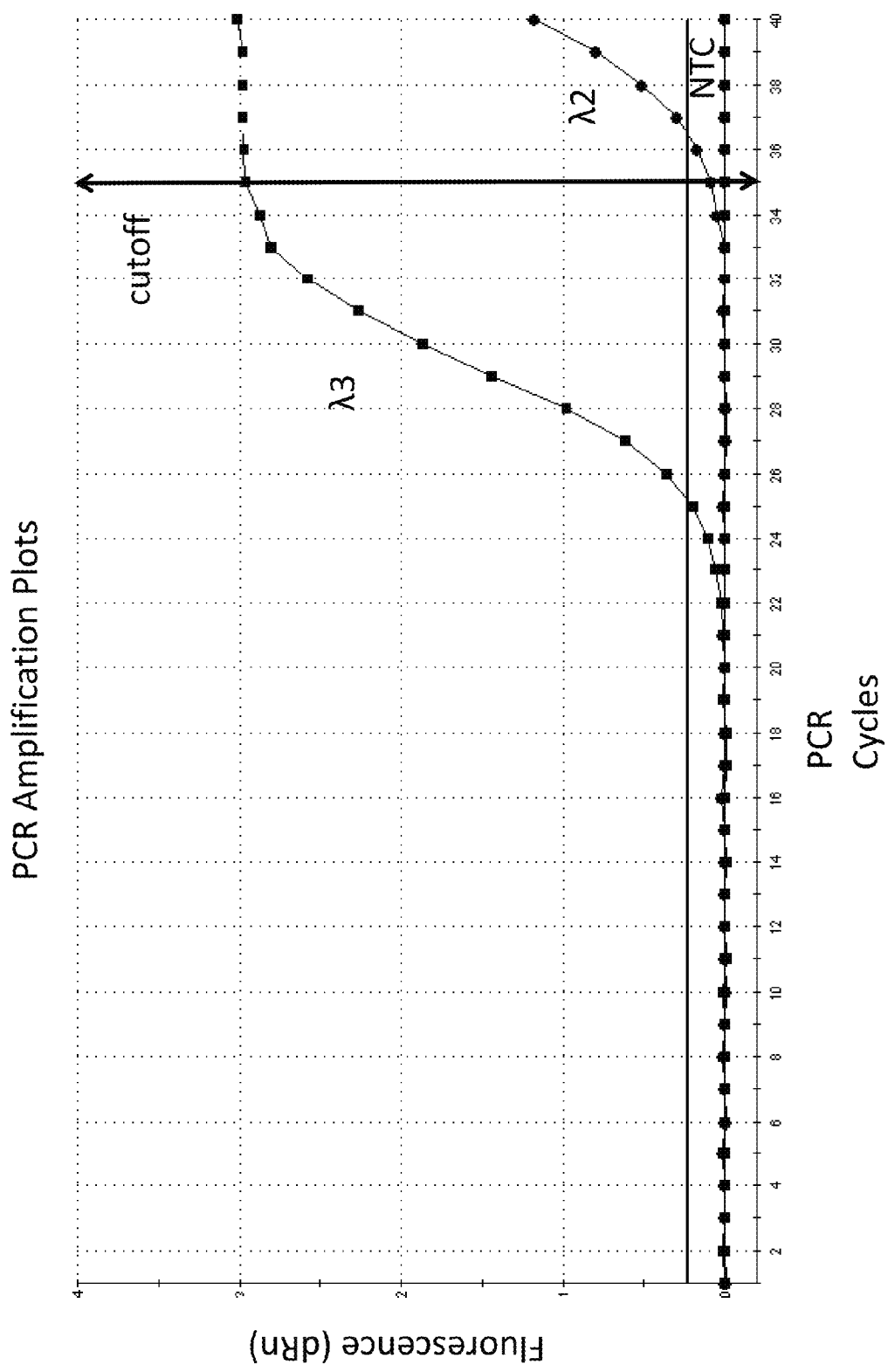

FIG. 16 depicts the specificity of the IFN-λ3 qRT-PCR. This figure shows the amplification of both IFN-λ3 (SEQ ID NO: 7) and IFN-λ2 (SEQ ID NO: 6) synthetic oligos by IFN-λ3 primers (forward, SEQ ID NO: 10; reverse, SEQ ID NO: 11). Note that $10^4$ copies of IFN-λ3 template is detectable at cycle 26, while amplification of the same amount of IFN-λ2 template is not detectable when the assay cutoff is set to 35 cycles and a fluorescence threshold of 0.225. These results demonstrate that the IFN-λ3 qRT-PCR is specific for IFN-λ3 and does not detect IFN-λ2 under the appropriate analysis parameters (i.e., discriminate IFN-λ3 from IFN-λ2). No amplification of the NTC was detected. Fluorescence is displayed as the change in the normalized reporter signal (dRn).

Figure 17:
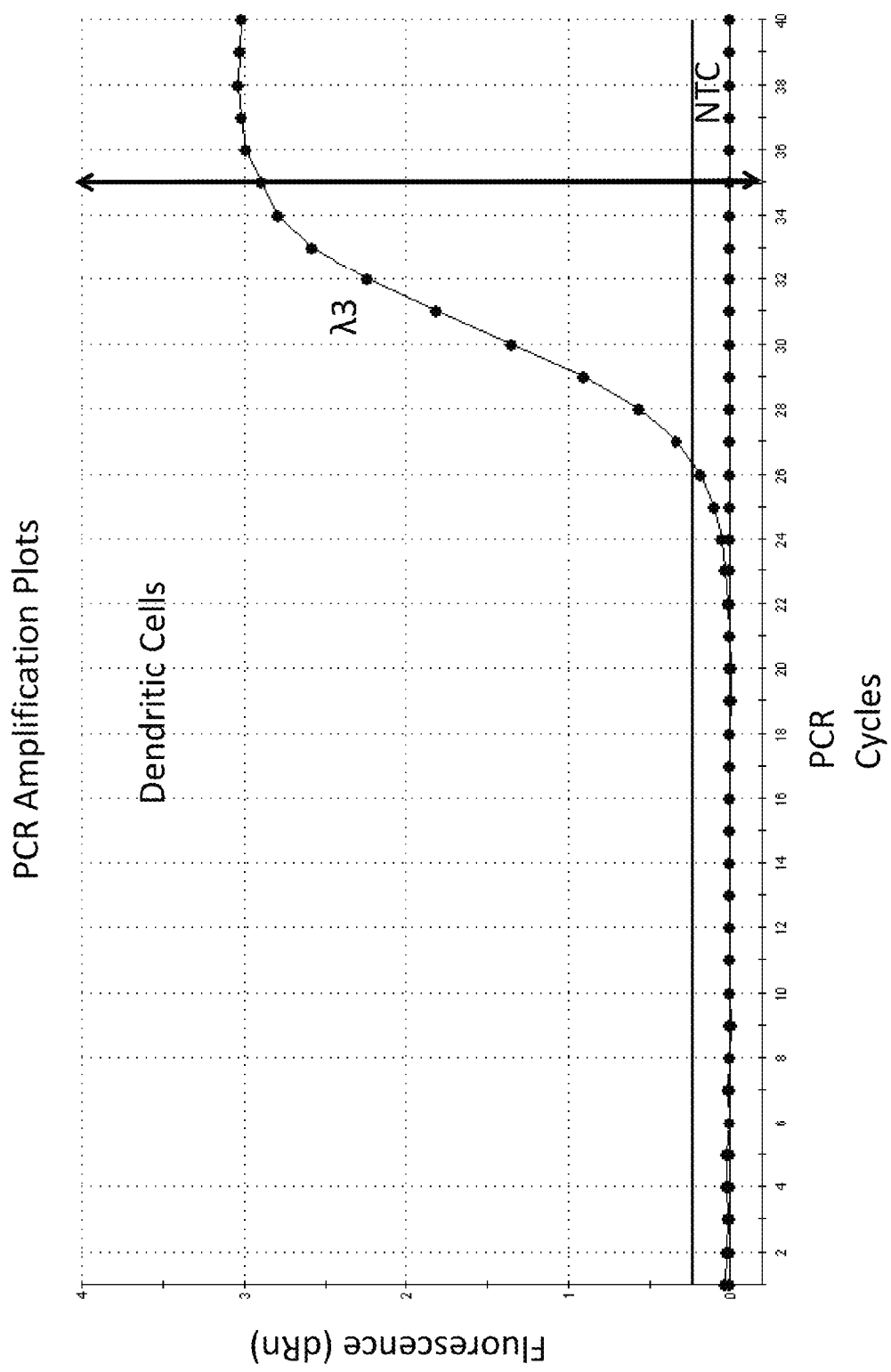

FIG. 17 depicts the detection of IFN-λ3 mRNA from virally-stimulated blood dendritic cells. Human pan-dendritic cells were isolated from peripheral blood mononuclear cells by magnetic selection. The resultant cells were cultured with HSV for 24 hours to stimulate production of IFN-λ, at which point mRNA was extracted using phenol-chloroform. cDNA was generated by reverse-transcriptase PCR and examined for the presence of IFN-λ3 transcripts by qRT-PCR. The PCR amplification plot depicts the amplification of IFN-λ3 mRNA harvested from freshly-isolated, in vitro-stimulated human blood derived dendritic cells, as opposed to synthetic IFN-λ3 oligonucleotides (SEQ ID NO: 7). Fluorescence is displayed as the change in the normalized reporter signal (dRn).

Figure 18:
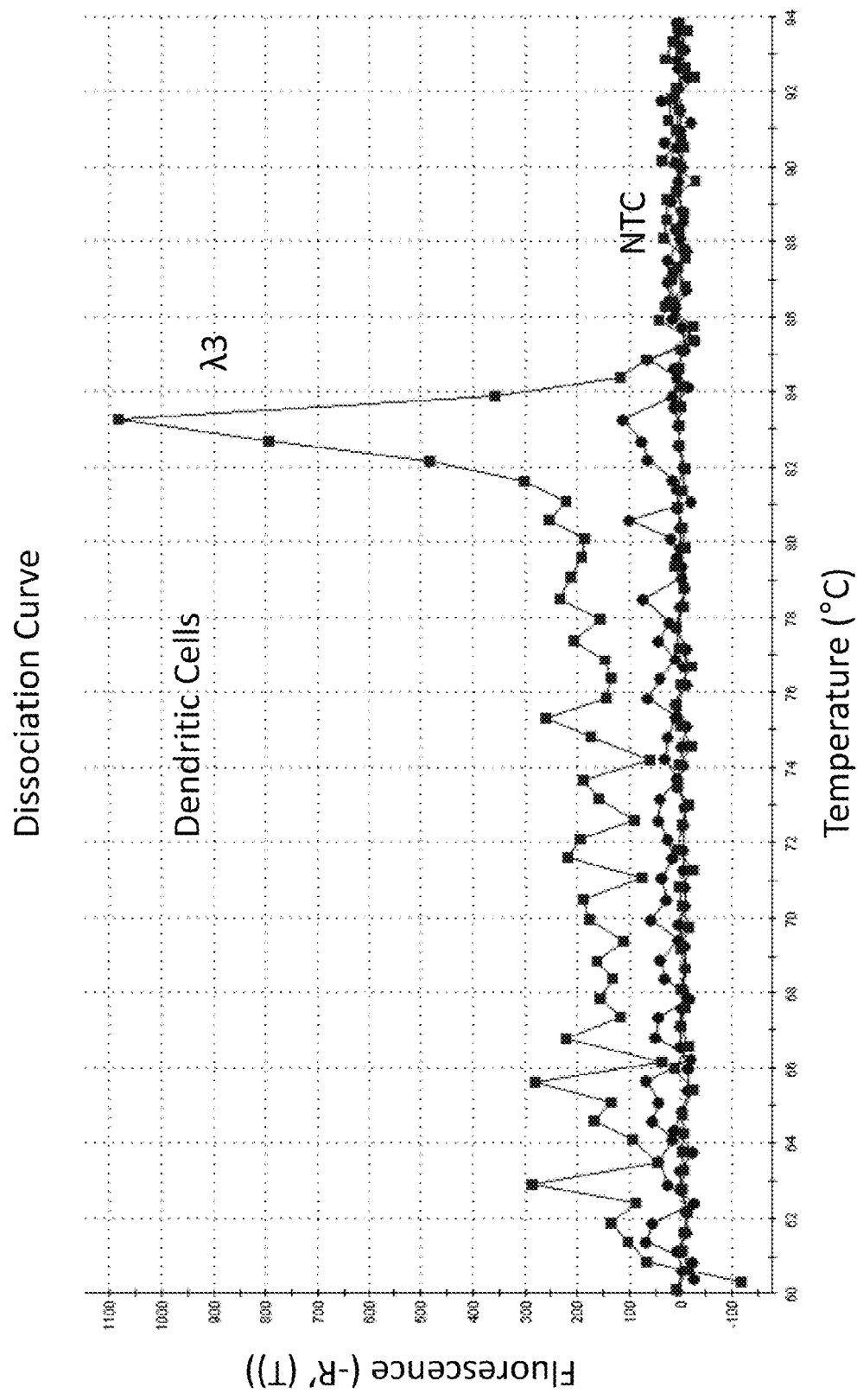

FIG. 18 depicts the dissociation curve of the amplicons generated in an IFN-λ3 qRT-PCR using dendritic cell cDNA. Note that the melting temperature of 83° C. matches that from the synthetic oligo amplicon. Fluorescence is shown as the negative of the decrease in fluorescence as a function of temperature (−R'(T)).

Figure 19:
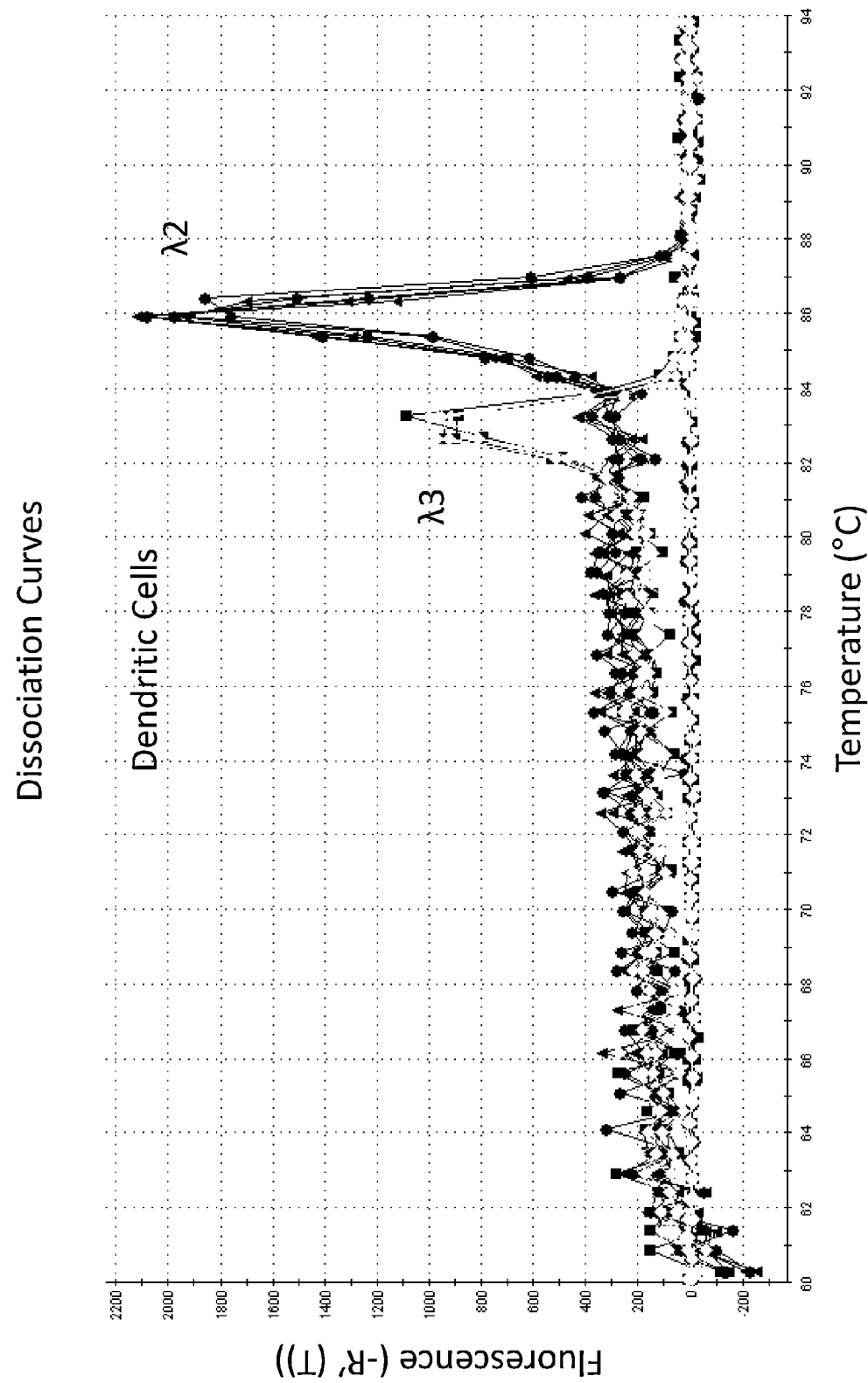

FIG. 19 depicts the overlay of the dissociation curve of the amplicons generated by the IFN-λ2 primers (forward, SEQ ID NO: 3; reverse, SEQ ID NO: 4) and IFN-λ3 primers (forward, SEQ ID NO: 10; reverse, SEQ ID NO: 11) using dendritic cell cDNA. This shows the different melting temperatures of the IFN-λ2 and IFN-λ3 amplicons indicating that they are distinct PCR products.

FIG. 20 depicts the sequence identity of the dendritic cell-derived IFN-λ3 amplicon (SEQ ID NO: 20) to that of the NCBI-deposited IFN-λ3 mRNA sequence (bases 339-419 of SEQ ID NO: 16). Analysis showed a 100% match between the dendritic cell amplicon and the deposited IFN-λ3 mRNA sequence.

FIG. 21 the binding region of an alternate set of IFN-λ3-specific primers (Set 2), which bind in the related region as the final working primers (Set 1). Primer Set 2 shares an identical reverse primer as Set 1 (i.e., SEQ ID NO: 11), and a forward primer (SEQ ID NO: 14) with two extra bases on the 5' end (5'-TGACCCAGCCCTGGGGGAT-3') as compared to that of SEQ ID NO: 10. Note that the addition of this two extra bases caused cross-reactivity with IFN-λ2 ablating the utility of the qRT-PCR.

Figure 22:
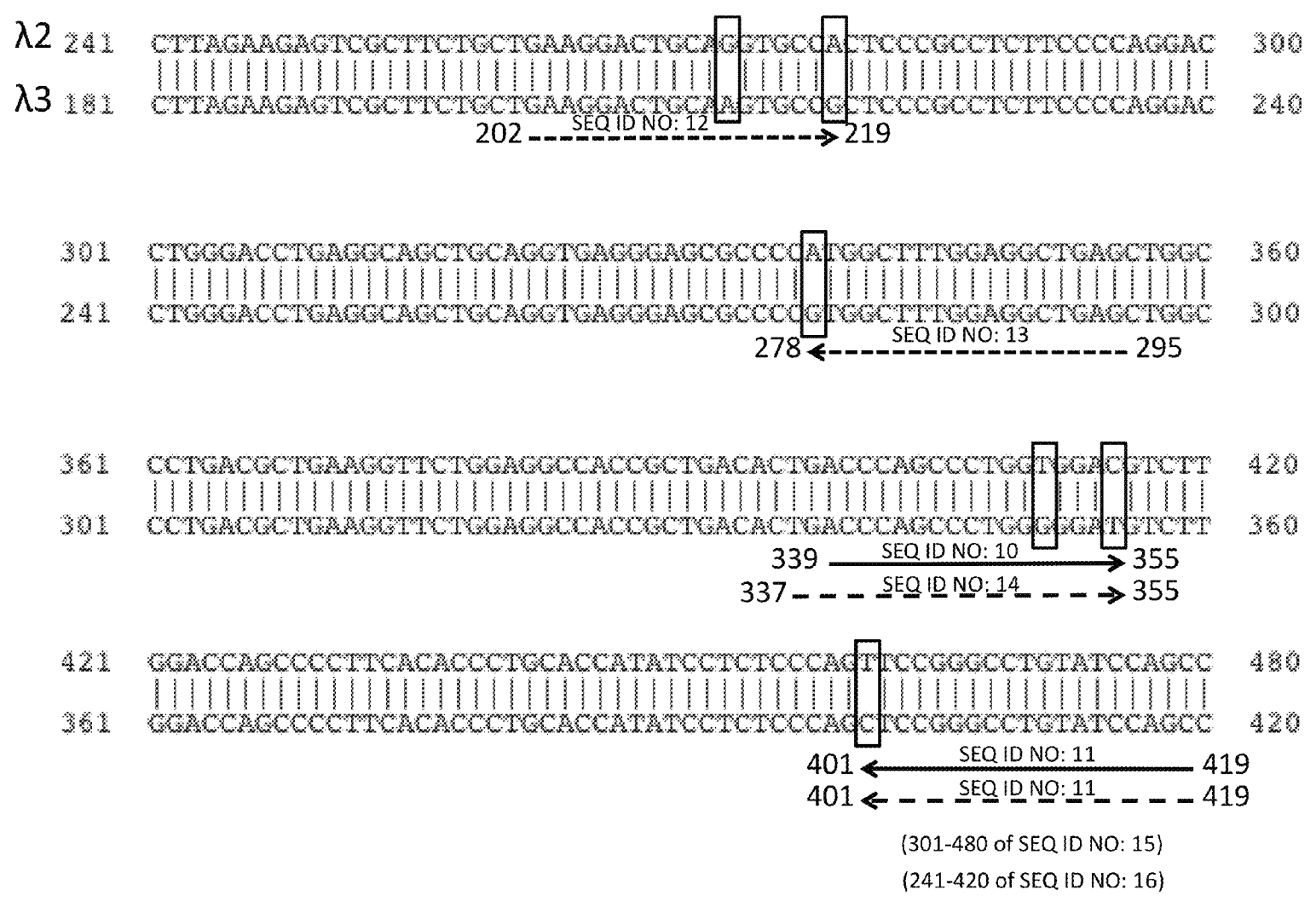

FIG. 22 depicts the binding region of an alternate set of IFN-λ3-specific primers (Set 3). Primer Set 3 spans non-homologous bases that are distinct from that of primer Set 1. Primer Set 3 binds bases 202-219 (forward; SEQ ID NO: 12) and 278-295 (reverse; SEQ ID NO: 13) produced amplification but also strong cross-reactivity with IFN-λ2. Forward primer sequence of SEQ ID NO: 12 is 5'-GAAGGACTGCAAGTGCCG-3'; reverse primer sequence of SEQ ID NO: 13 5'-CTCAGCCTCCAAAGCCAC-3'.

Figure 23:
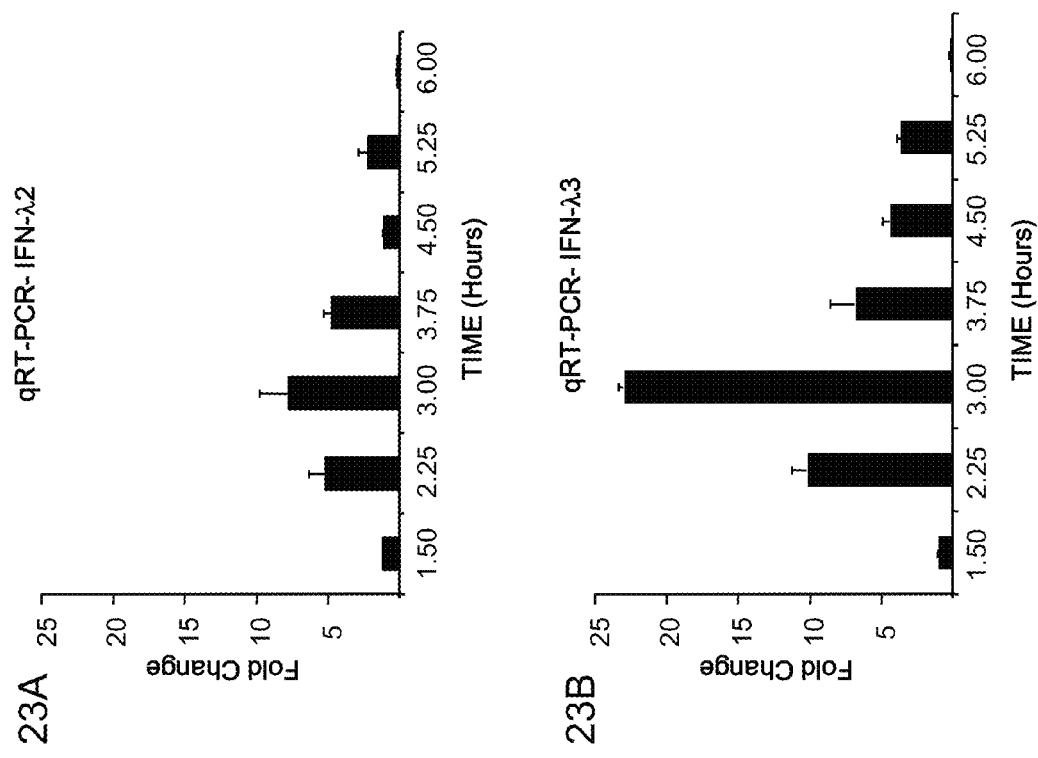

FIG. 23 depicts the detection of IFN-λ2 (FIG. 23A) or IFN-λ3 (FIG. 23B) mRNA from BEAS-2B bronchial epithelial cells stimulated with poly IC for up to 6 hours. Total RNA was extracted at the indicated time points. cDNA was generated using reverse-transcriptase and then was examined for the presence of IFN-λ2 (FIG. 23A) or IFN-λ3 (FIG. 23B) transcripts by qRT-PCR. The values depicted represent an average of triplicate measurements±SD.

Figure 24:
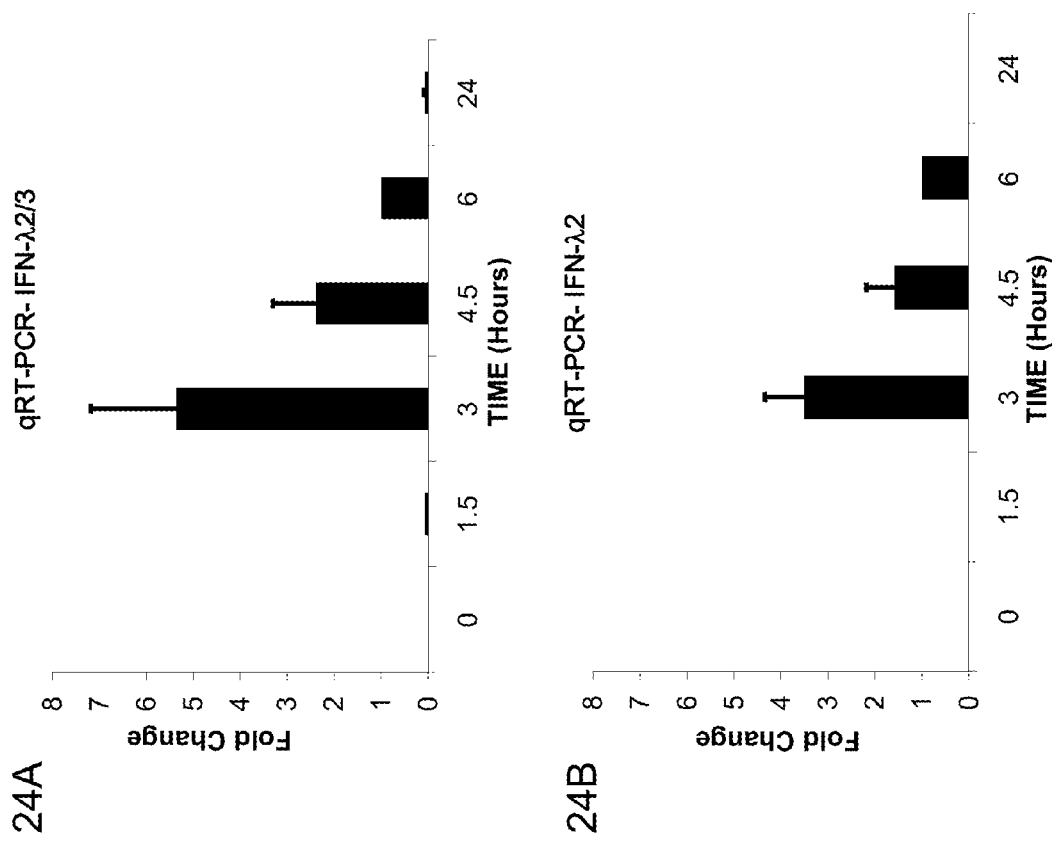

FIG. 24 depicts the detection of IFN-λ2/3 using a single non-specific primer set (FIG. 24A) or IFN-λ2 (FIG. 24B) mRNA from SW480 colon adenocarcinoma cells stimulated with poly IC for up to 24 hours. Total RNA was extracted at the indicated time points. cDNA was generated using reverse-transcriptase and then was examined for the presence of IFN-λ2/3 (FIG. 24A) or IFN-λ2 (FIG. 24B) transcripts by qRT-PCR. The values depicted represent an average of triplicate measurements±SD.

Figure 25:
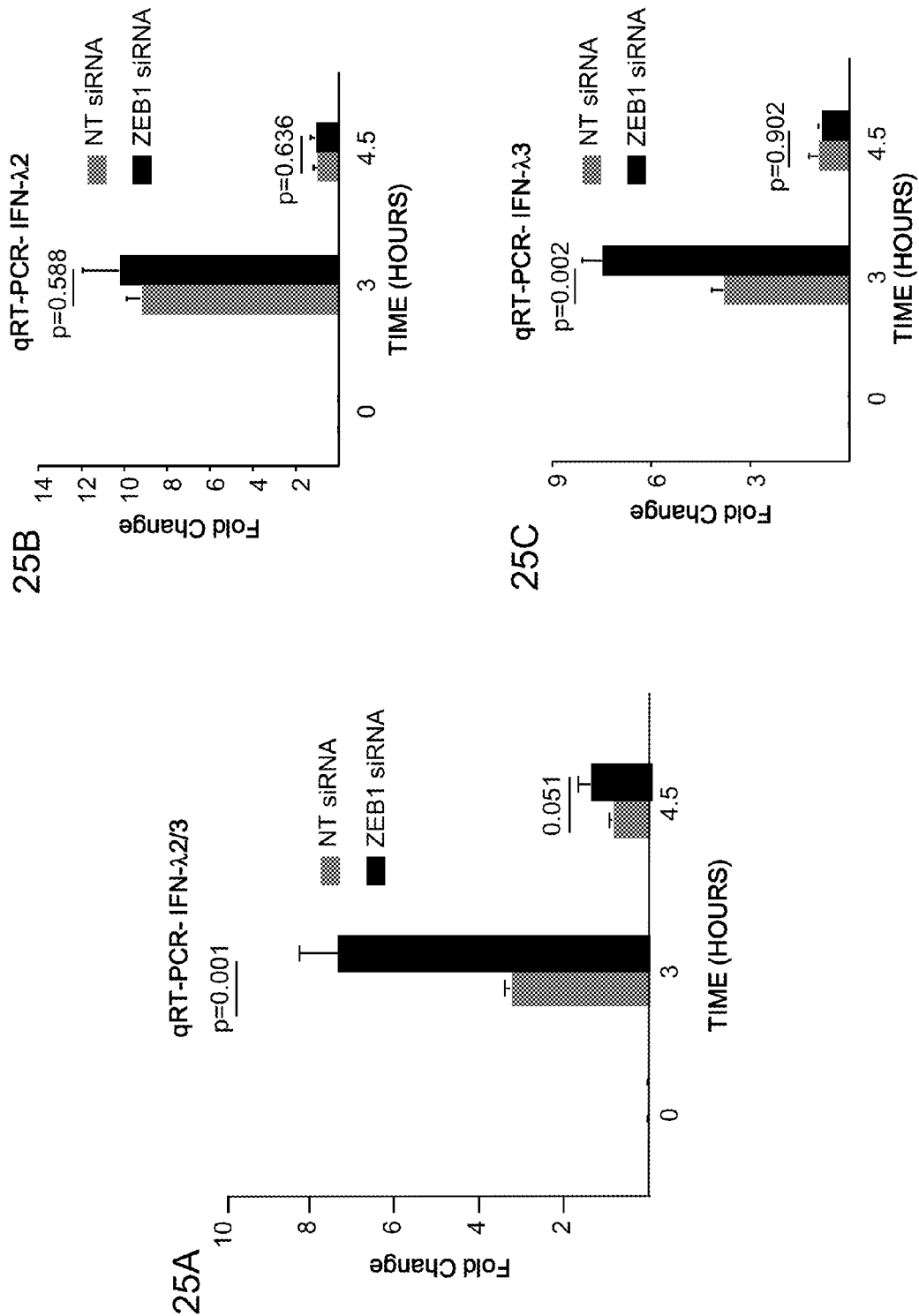

FIG. 25 depicts the effects of ZEB1 siRNA on IFN-λ expression in Beas-2B bronchial epithelial cells stimulated with poly IC (50 μg/mL) for up to 4.5 hours. Total RNA was prepared at the indicated time points.

FIG. 25A depicts IFN-λ2/3 mRNA expression as detected by qRT-PCR using a single non-specific primer set (SEQ ID NO: 17 and SEQ ID NO: 18). At 3 hours, ZEB1 siRNA treatment increases IFN-λ2/3 mRNA expression.

FIG. 25B depicts the effects of ZEB1 siRNA on IFN-λ2 mRNA expression as detected by qRT-PCR using the IFN-λ2 specific primer set (SEQ ID NO: 3 and SEQ ID NO: 4). ZEB1 siRNA treatment did not alter IFN-λ2 mRNA expression.

FIG. 25C depicts the effects of ZEB1 siRNA on IFN-λ3 mRNA expression as detected by qRT-PCR using the IFN-λ3 specific primer set (SEQ ID NO: 10 and SEQ ID NO: 11). At 3 hours, ZEB1 siRNA treatment increases IFN-λ3 mRNA expression. The values depicted represent an average of triplicate measurements±SD. Statistical analysis was performed using a Student's t-test; the p-values are indicated.

Figure 26:
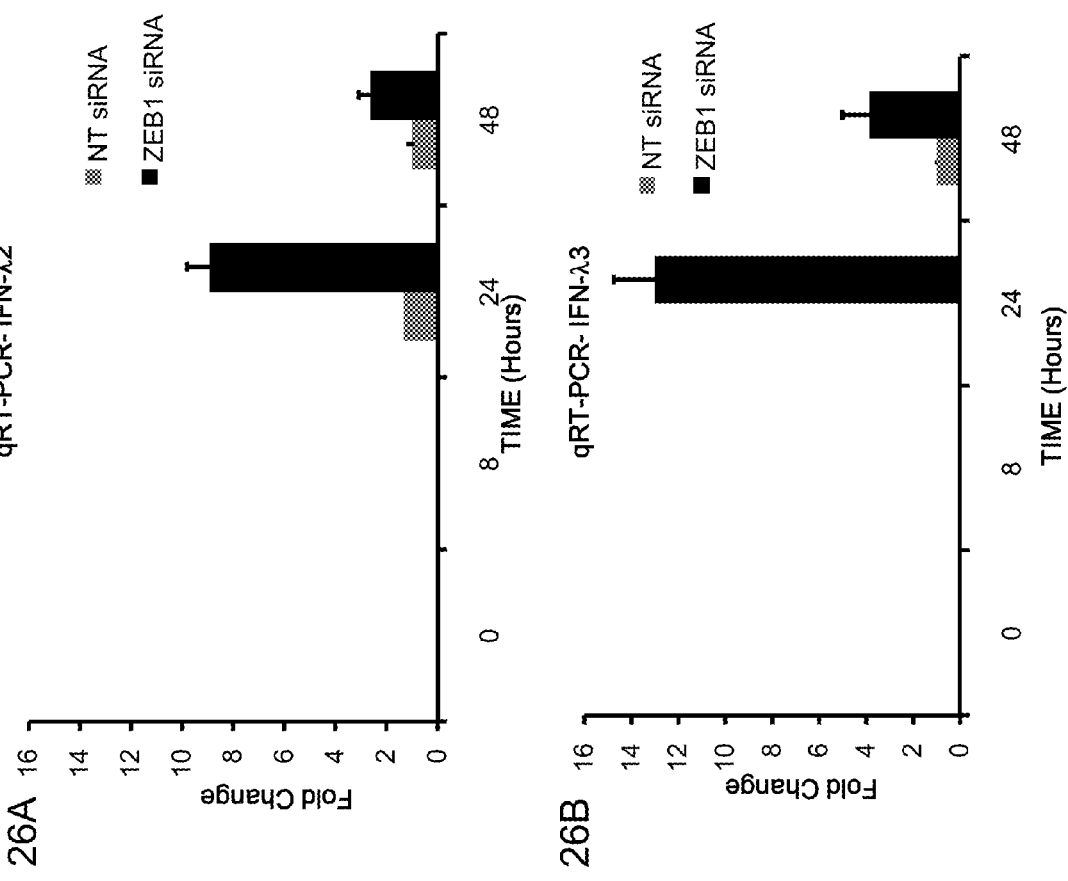

FIG. 26 depicts the effects of ZEB1 siRNA on IFN-λ expression in HEPG2 hepatocellular carcinoma cells infected with Human Rhinovirus Type 1 B. Total RNA was prepared following viral infection at the indicated time points.

FIG. 26A depicts the effects of ZEB1 siRNA on IFN-λ2 mRNA expression as detected by qRT-PCR using the IFN-λ2 specific primer set (SEQ ID NO: 3 and SEQ ID NO: 4). ZEB1 siRNA treatment led to increased IFN-λ2 mRNA expression at 24 hours and 48 hours post-infection.

FIG. 26B depicts the effects of ZEB1 siRNA on IFN-λ3 mRNA expression as detected by qRT-PCR using the IFN-λ3 specific primer set (SEQ ID NO: 10 and SEQ ID NO: 11). ZEB1 siRNA treatment led to increased IFN-λ3 mRNA expression at 24 hours and 48 hours post-infection. The values depicted represent an average of triplicate measurements±SD.

DETAILED DESCRIPTION OF THE INVENTION

The aspects, advantages and/or other features of example embodiments of the invention will become apparent in view of the following detailed description, taken in conjunction with the accompanying drawings. It should be apparent to those skilled in the art that the described embodiments of the present invention provided herein are merely exemplary and illustrative and not limiting. Numerous embodiments of modifications thereof are contemplated as falling within the scope of the present invention and equivalents thereto. All publications, patent applications, patents, and other references mentioned herein are incorporated by reference in their entirety.

Definitions:

As used herein, the term "biological sample" refers to a sample obtained from a human that contains mRNAs of IFN-λ2 or IFN-λ3. This includes, but is not limited to, a cell or tissue (a mixture of cells). For example, a cell may be a white blood cell, dendritic cell, epithelial cell, colon cell, liver cell and the like.

As used herein, the terms "interferon lambda" and "IFN-λ" are used interchangeably to describe a family of proteins that include IFN-λ1 (IL-29); IFN-λ2 (IL-28A); IFN-λ3 (IL-28B).

The term "IFN-λ1" refers to a protein of the helical cytokine family and is a type III interferon. It is also known as Interleukin-29 (IL-29). It is also known as IFNL-1. IFN-λ1 plays an important role in host defenses against microbes and its gene is highly up-regulated in cells infected with viruses. The IFN-λ1 gene is found on chromosome 19 in humans. Transcription of this gene directly results in a messenger RNA (mRNA) sequence that encodes the IFN-λ1 protein.

The term "IFN-λ2" refers to a protein the helical cytokine family and is a type III interferon. It is also known as "Interleukin-28A" (IL-28A). It is also known as IFNL-2. The IFN-λ2 gene is located near IL-29 on chromosome 19 in humans. Transcription of this gene directly results in a messenger RNA sequence that encodes the IFN-λ2 protein.

The term "IFN-λ3" refers to a protein the helical cytokine family and is a type III interferon. It is also known as "Interleukin-28B" (IL-28B). It is also known as IFNL-3. The IFN-λ3 gene is located near IL-29 on chromosome 19 in humans. Transcription of this gene directly results in a messenger RNA sequence that encodes the IFN-λ3 protein.

The nucleotide sequences encoding IFN-λs are known. The three IFN-λ mRNA sequences have been deposited in GenBank, the nucleotide sequences of which are incorporated by reference. The respective nucleotides sequences for IFN-λ2 and IFN-λ3 are set forth as follow:

```
IFN-λ2: GenBank Accession No: NM 172138.1
                                                          (SEQ ID NO: 15)
   1 tgggtgacag cctcagagtg tttcttctgc tgacaaagac cagagatcag gaatgaaact 61 agacatgact ggggactgca cgccagtgct ggtgctgatg gccgcagtgc tgaccgtgac 121 tggagcagtt cctgtcgcca ggctccacgg ggctctcccg gatgcaaggg gctgccacat 181 agcccagttc aagtccctgt ctccacagga gctgcaggcc tttaagaggg ccaaagatgc 241 cttagaagag tcgcttctgc tgaaggactc caggtgccac tcccgcctct tccccaggac 301 ctgggacctg aggcagctgc aggtgaggga gcgccccatg gctttggagg ctgagctggc 361 cctgacgctg aaggttctgg aggccaccgc tgacactgac ccagccctgg tggacgtctt 421 ggaccagccc cttcacaccc tgcaccatat cctctcccag ttccgggcct gtatccagcc 481 tcagcccacg gcagggccca ggacccgggg ccgcctccac cattggctgt accggctcca 541 ggaggcccca aaaaaggagt cccctggctg cctcgaggcc tctgtcacct tcaacctctt 601 ccgcctcctc acgcgagacc tgaattgtgt tgccagtggg gacctgtgtg tctgaccctc 661 ccaccagtca tgcaacctga gattttattt ataaattagc cacttgtctt aatttattgc 721 cacccagtcg ctat
```

-continued

IFN-λ3: GenBank Accession No: NM 172139.2

(SEQ ID NO: 16)

```
  1 agacatgacc ggggactgca tgccagtgct ggtgctgatg gccgcagtgc tgaccgtgac 61 tggagcagtt cctgtcgcca ggctccgcgg ggctctcccg gatgcaaggg gctgccacat 121 agcccagttc aagtccctgt ctccacagga gctgcaggcc tttaagaggg ccaaagatgc 181 cttagaagag tcgcttctgc tgaaggactg caagtgccgc tcccgcctct tccccaggac 241 ctgggacctg aggcagctgc aggtgaggga gcgccccgtg gctttggagg ctgagctggc 301 cctgacgctg aaggttctgg aggccaccgc tgacactgac ccagccctgg gggatgtctt 361 ggaccagccc cttcacaccc tgcaccatat cctctcccag ctccgggcct gtatccagcc 421 tcagcccacg gcagggccca ggacccgggg ccgcctccac cattggctgc accggctcca 481 ggaggcccca aaaaaggagt ccctggctg cctcgaggcc tctgtcacct tcaacctctt 541 ccgcctcctc acgcgagacc tgaattgtgt tgccagcggg gacctgtgtg tctga
```

The term "quantitative reverse transcription PCR" (i.e., "qRT-PCR") refers to a quantitative polymerase chain reaction (qPCR) used to detect mRNA expression levels. The qRT-PCR contains a first step wherein the mRNA molecules are converted to complementary DNA molecules (cDNAs) by reverse transcription enzyme in a "reverse transcription" reaction (RT). The qRT-PCR contains a second step wherein the expression levels of mRNA are quantified.

The terms "percent identity" refers to the percent of same nucleotides shared between two nucleotide sequences. For example, 96% identity between two gene sequences refers to 96% of the same nucleotides shared between the two gene sequences.

The term "interferon" refers to a group of secreted proteins that are produced by different cell types in response to various stimuli, such as exposure to a virus, bacterium, parasite, or other antigen, and that prevents viral replication in newly infected cells and, in some cases, modulates specific cellular functions.

The term "mRNA" refers to the template for protein synthesis; the form of RNA that carries the information from DNA in the nucleus to the ribosome for protein synthesis in the cell.

The term "transcription" refers to RNA synthesis, a process of creating an equivalent RNA copy of a sequence of DNA. A DNA sequence is read by RNA polymerase, which produces a complementary, anti-parallel RNA strand. Transcription is the first step leading to gene expression. If the gene transcribed encodes for a protein, the result of transcription is messenger RNA (mRNA), which will then be used to create that protein via the process of translation.

The term "siRNA" refers to a small interfering RNA (also known as, "short interfering RNA" or "silencing RNA"). RNA interference refers to the process of sequence-specific post-transcriptional gene silencing in animals mediated by short interfering RNA. siRNA is a class of double-stranded RNA molecules, usually but not exclusively, 20-25 nucleotides that are involved in the RNA interference (RNAi) pathway, where it interferes with the expression of a specific gene. siRNA oligonucleotides target the mRNA for degradation via sequence-specific complementary base pairing such that the target mRNA is recognized by the siRNA that has been incorporated into an RNA-induced silencing complex (RISC). Once recognized by the RISC complex, the targeted mRNA is then degraded by RNase-mediated cleavage in P-body cytoplasmic compartment (reviewed in Wu and Belasco, 2008).

The term "HSV" refers to herpes simplex virus. There are two members of the herpes virus family (HSV1 and HSV2), Herpesviridae, that infect humans. Both HSV-1 (which produces most cold sores) and HSV-2 (which produces most genital herpes) are ubiquitous and contagious. They can be spread when an infected person is producing and shedding the virus.

The term "dendritic cells" refers to a subset of leukocytes (white blood cells), whose function is to present antigen in the immune system. These cells respond to the presence of pathogens, such as viral pathogens, by transcribing immune response genes (such as IFN-λ genes) into mRNA and translating the mRNA to protein (such as IFN-λ proteins), and secreting them to influence adjacent cells.

The term "amplicon" refers to a fragment of double-stranded DNA or RNA that is the source and/or product of natural or artificial amplification or replication events. It can be formed using various methods including polymerase chain reactions (PCR), ligase chain reactions (LCR), or natural gene duplication. As the product of an amplification reaction, amplicon is used interchangeably with common laboratory terms, such as PCR product.

The term "amplification" refers to the production of one or more copies of a genetic fragment or target sequence, specifically the amplicon.

The term "dissociation curve" refers to a method of determining the unique nature of an amplicon, wherein the amplicon is heated until its two DNA strands separate. As the temperature increases, the DNA strands dissociate and UV absorbance intensifies. An amplicon comprising a single product will give a sharply-defined single peak. Thus, the fidelity of any PCR reaction can be inferred by the presence of one or more peaks in the dissociation curve.

The term "synthetic oligonucleotide" (i.e., "synthetic oligo") refers to a short, single-stranded DNA or RNA molecule (typically, but not exclusively, 15-25 nucleotides in length). Often, such synthetic oligos are used to prime DNA synthesis reactions, such as PCR reactions.

The term "BEAS-2B bronchial epithelial cells" refers to a perpetual human bronchial epithelial cell-line derived, described and defined by the American Type Culture Collection, Catalog no. CRL-9609.

The term "SW480 colon adenocarcinoma cells" refers to a perpetual human colon adenocarcinoma cell-line derived, described and defined by the American Type Culture Collection catalog number CCL-228.

The term "TLR3 agonist" (toll-like receptor (TLR)3 agonist" refers to a natural or synthetic compound, molecule or other entity able to interact with TLR3 in a way that triggers a response equivalent to that resulting from interaction between TLR3 and a pathogen-related ligand, typically but not exclusively double-stranded RNA, and consequently causing gene expression (such as IFN-λ genes).

The term "poly IC" refers to polyinosinic:polycytidylic acid which is an immunostimulant. It is used in the form of a sodium salt to simulate viral infections. Poly IC is known to interact with TLR3. It is structurally similar to double-stranded RNA, which is present in some viruses and is a "natural" stimulant of TLR3. Thus, it can be considered a synthetic analog of double-stranded RNA and is a common tool for scientific research on the immune system.

The term "transfected" refers to the deliberate introduction of a nucleic acid into cells.

The term "transfection" refers to a process by which agents (such as IFN-λ1 reporter constructs or siRNAs) are introduced into a cell (such as a mammalian cell). The transfection methods include, but not limited to, calcium phosphate-based transfection, DEAE-dextran-based transfection, lipid-based transfection, molecular conjugate-based transfection (e.g. polylysine-DNA conjugates), electroporation, microinjection and the like.

The term "cDNA" refers to DNA synthesized from a messenger RNA (mRNA) template in a reaction catalyzed by the enzyme reverse transcriptase. cDNA is used to clone eukaryotic genes in prokaryotes.

The term "ZEB1" refers to the zinc finger E-box binding homeobox 1 gene that encodes a zinc finger transcription factor. This zinc finger transcription factor is also referred to with multiple names such as: AREB6, DELTA-EF12, TCF8, NIL-2A2, and ZFHEP2.

The term "HEPG2 hepatocellular carcinoma cells" refers a hepatoma cell line derived, described and defined by the American Type Culture Collection catalog no. HB-0865.

The term "Rhinovirus Type 1B" is a serotype of the twelve species of the enterovirus genus. Rhinoviruses are the most suspected causative agents of the common cold.

The present invention relates to primers, probes, assay kits and methods for identifying and distinguishing between IFN-λ2 and IFN-λ3 mRNA. In one aspect, the present invention provides a highly sensitive and specific quantitative reverse transcription PCR (qRT-PCR) assay to detect and quantify each of the mRNA for IFN-λ subtypes (i.e., IFN-λ subtypes 2 and 3).

Methods include providing a biological sample of a human and performing a qRT-PCR analysis of the biological sample. The biological sample may include for example, isolated RNA such as mRNA, and cells obtained and isolated from a human including, but not limited to, epithelial cells, colon cells, bronchial cells, liver cells, cancer cells and the like. Cells can be isolated from a human using standard protocol. For example, leukocytes can be isolated from blood using Hypaque Ficoll. Specific cells (i.e., dendritic cells) can also be isolated using magnetic beads that are known to one skilled in the art. mRNA can be extracted and isolated from a mammal according to known methods. Standard extraction methods include the use of a chemical agent such as guanidinium thiocyanate, phenol-chloroform extraction, guanidine-based extraction, and the like. Commercial nucleic acid extraction kits may be employed. For example, RNeasy Fibrous Tissue Mini Kit from Qiagen (Valencia, Calif.) and RNAimage Kit from GenHunter Corporation (USA). qRT-PCR analysis of the biological sample may be performed on the biological sample obtained form a human.

According to non-limiting example embodiments, the PCR analysis of the biological sample may be a qRT-PCR assay where mRNA is first isolated from a biological sample followed by qRT-PCR on the isolated mRNA. The present invention provides the use of qRT-PCR to detect and quantify the expression level of IFN-λ2 or IFN-λ3 mRNA. qRT-PCR (quantitative reverse transcription-polymerase chain reaction) is a sensitive technique for mRNA detection and quantitation. Compared to Northern blot analysis and RNase protection assay, qRT-PCR can be used to quantify mRNA levels from much smaller samples. qRT-PCR allows the quantitation of PCR products using a housekeeper gene as a reference. Preferably, the housekeeper gene is GADPH.

qPCR using a cDNA template is a PCR assay in a single reaction with the use of PCR probes or primers, each specific for its own target and comprising a fluorescent moiety that emits at a unique wavelength. qRT-PCR may be performed using real-time PCR including TaqMan® probes, Molecular Beacons, and Scorpions, as recognized by one skilled in the art. SYBR® Green may also be amenable to qRT-PCR.

Typically, a qRT-PCR reaction is quantified by comparison to a standard curve or comparison of threshold cycle (Ct) values. In the first of these methods, a standard curve of amplification products of a particular cDNA is made based on amplification of a series of different, known amounts of a pre-selected nucleic acid. Amplification results of reactions performed on a target nucleic acid are then compared to the standard curve to obtain a quantity, and that quantity can be extrapolated to an amount of the target in the original sample. In the Ct comparison method for quantitating PCR products, expression of a housekeeping gene (such as GADPH) is used as a standard against which amplification of a target nucleic acid is compared. Often, in this method, a comparison of expression of the target nucleic acid under two different conditions is performed to determine changes in expression patterns.

In one embodiment, real-time PCR may be performed using exonuclease primers (TaqMan® probes). In such embodiment, the primers utilize the 5' exonuclease activity of thermostable polymerases such as Taq to cleave dual-labeled probes present in the amplification reaction (See, e.g., Wittwer, C. et al. *Biotechniques* 22:130-138, 1997). While complementary to the PCR product, the probes used in this assay are distinct from the PCR primers and are dually-labeled with both a molecule capable of fluorescence and a molecule capable of quenching fluorescence. When the probes are intact, intramolecular quenching of the fluorescent signal within the DNA probe leads to little signal. When the fluorescent molecule is liberated by the exonuclease activity of Taq during amplification, the quenching is greatly reduced leading to increased fluorescent signal. Non-limiting example fluorescent probes include 6-carboxy-floruescein moiety and the like. Exemplary quenchers include Black Hole Quencher 1 moiety and the like. Real-time polymerase chain reaction enables one to amplify and simultaneously quantify a targeted DNA molecule (i.e., IFN-2 or 3). It enables both detection and quantification (as absolute number of copies or relative amount when normalized to DNA input or additional normalizing genes) of one or more specific sequences in a DNA sample. Currently at least four (4) different chemistries, TaqMan® (Applied Biosystems, Foster City, Calif.), Molecular Beacons, Scorpions® and SYBR® Green (Molecular Probes), are available for real-time PCR.

All of these chemistries allow detection of PCR products via the generation of a fluorescent signal. TaqMan probes, Molecular Beacons and Scorpions depend on Förster Resonance Energy Transfer (FRET) to generate the fluorescence signal via the coupling of a fluorogenic dye molecule and a quencher moiety to the same or different oligonucleotide substrates. SYBR Green is a fluorogenic dye that exhibits little fluorescence when in solution, but emits a strong fluorescent signal upon binding to double-stranded DNA.

Two common methods for detection of products in real-time PCR are: (1) non-specific fluorescent dyes that intercalate with any double-stranded DNA, and (2) sequence-specific DNA probes consisting of oligonucleotides that are labeled with a fluorescent reporter which permits detection only after hybridization of the probe with its complementary DNA target.

Real-time PCR, when combined with reverse transcription, can be used to quantify messenger RNA (mRNA) in cells or tissues. An initial step in the reverse transcription PCR amplification is the synthesis of a DNA copy (i.e., cDNA) of the region to be amplified. Reverse transcription can be carried out as a separate step, or in a homogeneous reverse transcription-polymerase chain reaction (RT-PCR), a modification of the polymerase chain reaction for amplifying RNA. Reverse transcriptases suitable for synthesizing a cDNA from the RNA template are well known. Following the cDNA synthesis, methods suitable for PCR amplification of ribonucleic acids are known in the art (See, Romero and Rotbart in Diagnostic Molecular Biology: Principles and Applications pp. 401-406). PCR reagents and protocols are also available from commercial vendors, such as Roche Molecular Systems. PCR can be performed using an automated process with a PCR machine.

The present invention advantageously allows amplification and detection of the respective IFN-λ2 and IFN-λ3 mRNA subtypes, both with similar high sensitivity. Notably there are only a total of 11 mismatches between IFN-λ2 mRNA and IFN-λ3 mRNA. The present inventors unexpectedly discovered that only highly restricted and specific regions on IFN-λ2 mRNA and IFN-λ3 mRNA are permitted for the design of primer/probe sets (complementary to the mRNAs) that allow one to perform a PCR reaction that will amplify, detect, quantify, and discriminate IFN-λ2 and IFN-λ3 mRNA in a quantitative manner. The present inventors surprisingly noted that a slight change in the location or length of the primer/probe sets can drastically affect their ability to amplify, detect, and discriminate IFN-λ2 or IFN-λ3.

In one aspect, the present invention provides a method of using unique primers/probes as a diagnostic kit that has utility in the diagnosis of diseases. The diagnostic kit and its associated primer/probe sets can be used to establish expression patterns of IFN-λ2 and IFN-λ3 mRNA subtypes that are associated with various diseases, including infections, autoimmunity and cancer. Identifying various patterns of IFN subtype expression can also be used to monitor the treatment of various autoimmune diseases and chronic infections, or tumor therapy and the like.

In one embodiment, the forward primer and the reverse primer for specific detection of IFN-λ2 mRNA (not IFN-λ3 mRNA) are SEQ ID NO: 3 and SEQ ID NO: 4, respectively.

In another embodiment, the forward primer and the reverse primer for specific detection of IFN-λ3 mRNA (not IFN-λ2 mRNA) are SEQ ID NO: 10 and SEQ ID NO: 11, respectively.

In another embodiment, the present PCR kit provides an amplification reaction that has high efficiency and specific-ity. The present assay has sensitivity sufficient to detect at least about 1-10 copies of the sequence encoding the IFN-λ2 or IFN-λ3 mRNA subtype of interest per PCR reaction. The present assay also has a high specificity to discriminate between IFN-λ2 mRNA and IFN-λ3 mRNA (i.e., at least about a 5 cycle number difference between specific and nonspecific amplification).

In another embodiment, the PCR reaction uses conditions comprising: Stage 1: 50° C. for two minutes; Stage 2: 95° C. for three minutes; and Stage 3: 40 repeats of 95° C. for 15 seconds followed by 59° C. for one minute.

In another embodiment, the present qRT-PCR kit may comprises a plurality of forward primers and reverse primers in a single multiplex reaction vessel, wherein each set of forward primer and reverse primer together enables specific amplification of a sequence encoding a single IFN-λ subtype (i.e., either IFN-λ2 or IFN-λ3) from a composition comprising a plurality of IFN-λ subtype templates. Further provided herein are kits for performing the methods provided herein, including methods for detecting and distinguishing IFN-λ2 or IFN-λ3 mRNAs. The kits may include for example one or more of the primers or primer pairs provided herein. Example kits may include instructions for using primer pairs in qRT-PCR reactions to determine if a biological sample obtained from a human contains IFN-λ2 mRNA, or IFN-λ3 mRNA, or both.

In another embodiment, the present invention provides a method of detecting the presence of at least one of the IFN-λ2 or IFN-λ3 mRNA subtype of interest in a sample comprising: a) contacting a sample with primer set specific for IFN-λ2 or IFN-λ3 under conditions suitable for amplification of the nucleic acid sequence of the IFN-λ2 or IFN-λ3 subtype of interest; and b) detecting an amplification product for the IFN-λ2 or IFN-λ3 subtype of interest, wherein the presence of the amplification product indicates that the IFN-λ2 or IFN-λ3 subtype of interest is present in the sample.

In another embodiment, the invention provides a method of monitoring the efficacy of a treatment for a disease condition comprising: a) contacting a sample with primer set specific for IFN-λ2 or IFN-λ3 under conditions suitable for amplification of the nucleic acid sequence of the IFN-λ2 or IFN-λ3 subtype of interest; b) detecting an amplification product for the IFN-λ2 or IFN-λ3 subtype of interest; and c) generating an expression profile for the at least one IFN-lambda subtype of interest, wherein the presence of the amplification product indicates that the IFN-λ2 or IFN-λ3 subtype of interest is present in the sample.

The present invention will be better understood from the following experimental studies. One of ordinary skill in the art would readily appreciate that the specific methods and results discussed therein are not intended to limit the invention. The experimental studies merely serve illustrative purposes, and the invention is more fully described by the claims that follow thereafter.

EXPERIMENTAL STUDIES

Example 1

Sequence Alignment Between Human IFN-λ2 mRNA and IFN-λ3 mRNA and Identification of Potential PCR Primer Sites We conducted a sequence alignment analysis using publically available sequence information from NCBI by blasting nucleotide sequences between human IFN-λ2 (accession no. NM_172138.1) and IFN-λ3 (accession no. NM_172139.2). The mRNA sequences of IFN-λ2 and IFN-λ3 in human exhibit a 98% identity. Given such a high degree of identity, it is commonly known to be extremely difficult to distinguish these two mRNAs by routine molecular assays such as qRT-PCR. In other words, it is very difficult to identify unique primer pairs that are specific for one mRNA but not for the other.

PCR Templates

IFN-λ2: In order to develop a qRT-PCR assay, we first chemically synthesized a oligonucleotide fragment (oligo) that is identical to that of human IFN-λ2 mRNA between 242 to 391 base pairs (See, FIG. 3). The oligo is 150 nucleotides in length (SEQ ID NO: 1). We used this prepared oligonucleotide fragment (SEQ ID NO: 1) as the PCR templates to perform qRT-PCR assays.

IFN-λ3: We also chemically synthesized the oligonucleotide template for IFN-λ3. The chemical synthesized IFN-λ3 oligonucleotide fragment (oligo) that is 150 nucleotides in length, and has nucleotide sequences that are identical to that of human IFN-λ3 mRNA between 182 to 337 base pairs (SEQ ID NO: 2) (See, FIG. 3).

In this first series of study, we designed a forward PCR primer between bases 262 and 279 of sequence 5'-GAAGGACTGCAGGTGCCA-3' (SEQ ID NO: 3) which is seventeen (17) nucleotides in length and spanning the region of IFN-λ2 mRNA that contains the two (2) non-homologous base pairs (i.e., to utilize the two (2) non-homologous base pairs (i.e., G-A and A-G)) (See, FIG. 2). We also designed a reverse PCR primer between 338 and 355 of sequence 5'-CTCAGCCTCCAAAGCCAT-3' (SEQ ID NO: 4) which is eighteen (18) nucleotides in length and spanning the region of IFN-λ2 mRNA that contains the one (1) non-homologous base pair (i.e., to utilize one non-homologous base pair (i.e., A-G) (See, FIG. 2). We designed this PCR primer set specifically to examine the suitability of generating IFN-λ2-specific primers that would bind to IFN-λ2 mRNA in a region that is not homologous with IFN-λ3 mRNA (See, FIG. 2).

Figure 4:
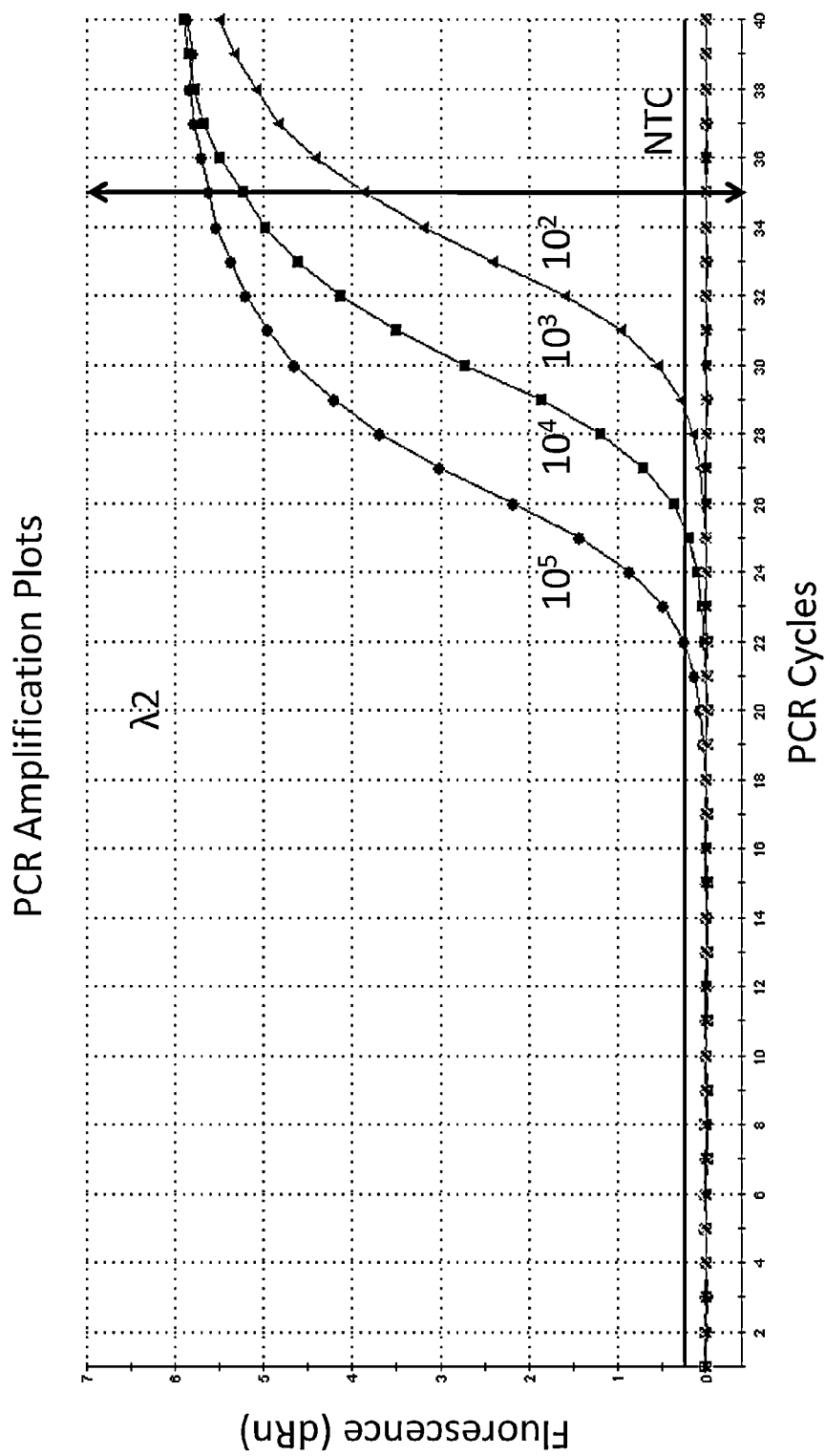
FIG. 4 depicts the sensitivity of qRT-PCR for the IFN-λ2. The figure depicts amplification plots of the IFN-λ2-specific qRT-PCR, using ten-fold dilutions of the IFN-λ2 synthetic oligo (SEQ ID NO: 1) as a template in the PCR. The resultant amplification plots demonstrate dose dependent amplification, down to 100 copies of template. No amplification of the template control (NTC) was detected. Fluorescence is displayed as the change in the normalized reporter signal (dRn).

Using the primer pair (forward: SEQ ID No: 3 and reverse: SEQ ID NO: 4) and PCR template (SEQ ID NO: 1), we observed a dose-dependent amplification of IFN-λ2, ranging from $10^2$ to $10^5$ copies of the oligonucleotide fragment templates (FIG. 4). Note that there was no PCR signal when no oligonucleotide fragment was used as template (i.e., NTC; "no template control" was used). This study confirms that the designed PCR primer set is able to amplify, based on the oligonucleotide templates, to produce an IFN-λ2 amplicon.

Example 2

Dissociation Curve Analysis

In this study, we conducted a dissociation curve analysis using MxPro Software (Agilent Technologies). Dissociation curve analysis is to make advantage of the melting characteristics of a double-stranded DNA. The principle is based on the fact that while the G-C base pairings have three (3) hydrogen bonds, the A-T pairings have only two (2) hydrogen bonds. A greater amount of heat is therefore needed to dissociate a G-C pairing as opposed to an A-T pairing. Amplicons having a higher G-C content will have a higher melting temperature as compared to that of a lower G-C content (i.e., A-T rich).

Using the dissociation curve analysis, we determined if our selected PCR primer pair (i.e., SEQ ID NOs: 3 and 4, in Example 2) only yields one (1) amplicon in our qRT-PCR assay (i.e., specific to IFN-λ2 and not IFN-λ3). The generation of one single peak in the dissociation curve indicates the production of one (1) single amplicon, while the generation of multiple peaks reveals more than one (1) amplicon.

Figure 5:
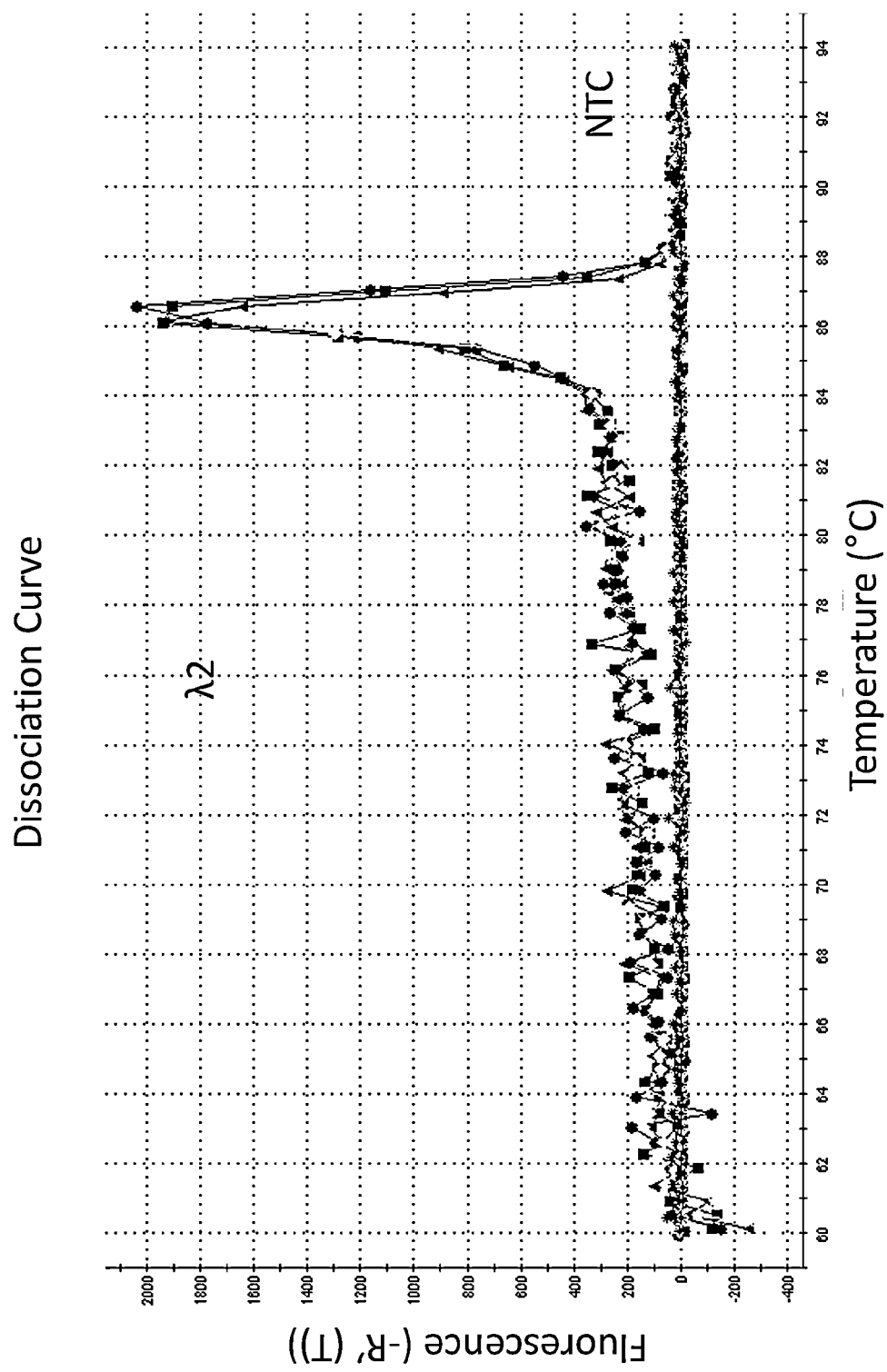
FIG. 5 depicts the dissociation curve (i.e., melting curve) of the single amplicon produced from the IFN-λ2 oligo (SEQ ID NO: 1). The melting temperature is shown to be 86° C. Fluorescence is shown as the negative of the decrease in fluorescence as a function of temperature (−R'(T)).

As shown in FIG. 5, we detected only one (1) single amplicon at 86° C., thus demonstrating that our qRT-PCR is specific to IFN-λ2 and not IFN-λ3. The dissociation curve analysis verifies the suitability of our IFN-λ2-specific primers used in conjunction with our qRT-PCR assay to distinguish between IFN-λ2 and IFN-λ3 mRNAs.

Example 3

Figure 1:
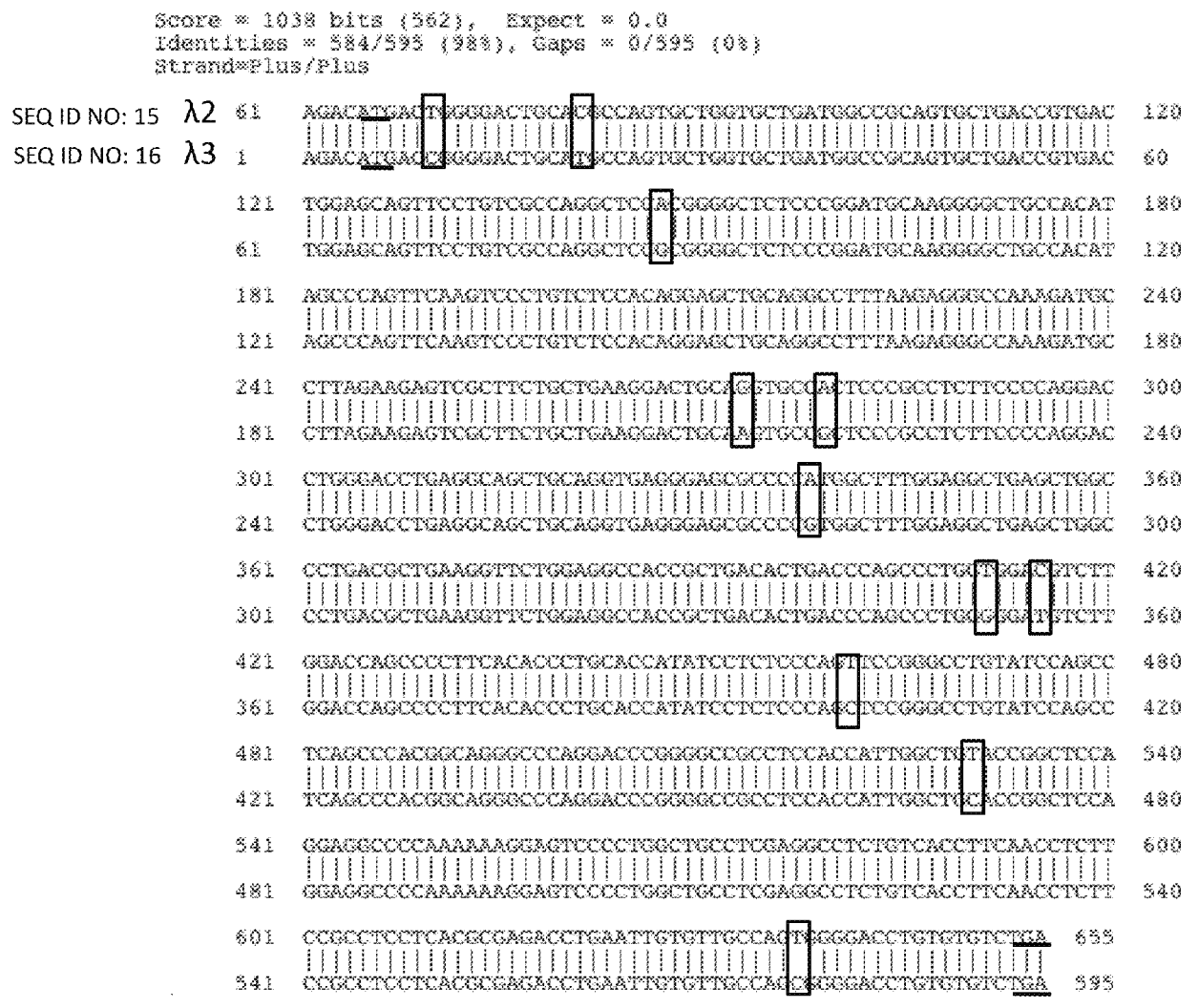

Cross-Reactivity Study of IFN-λ2 Primers ur sequence alignment study revealed that IFN-λ2 and IFN-λ3 are highly homologous at the nucleotide level (See, Example 1, and FIG. 1). To show specificity, it is important to determine that the selected primers would amplify IFN-λ2 in our qRT-PCR assay but not IFN-λ3 (i.e., no cross-reactivity with IFN-λ3).

Figure 6:
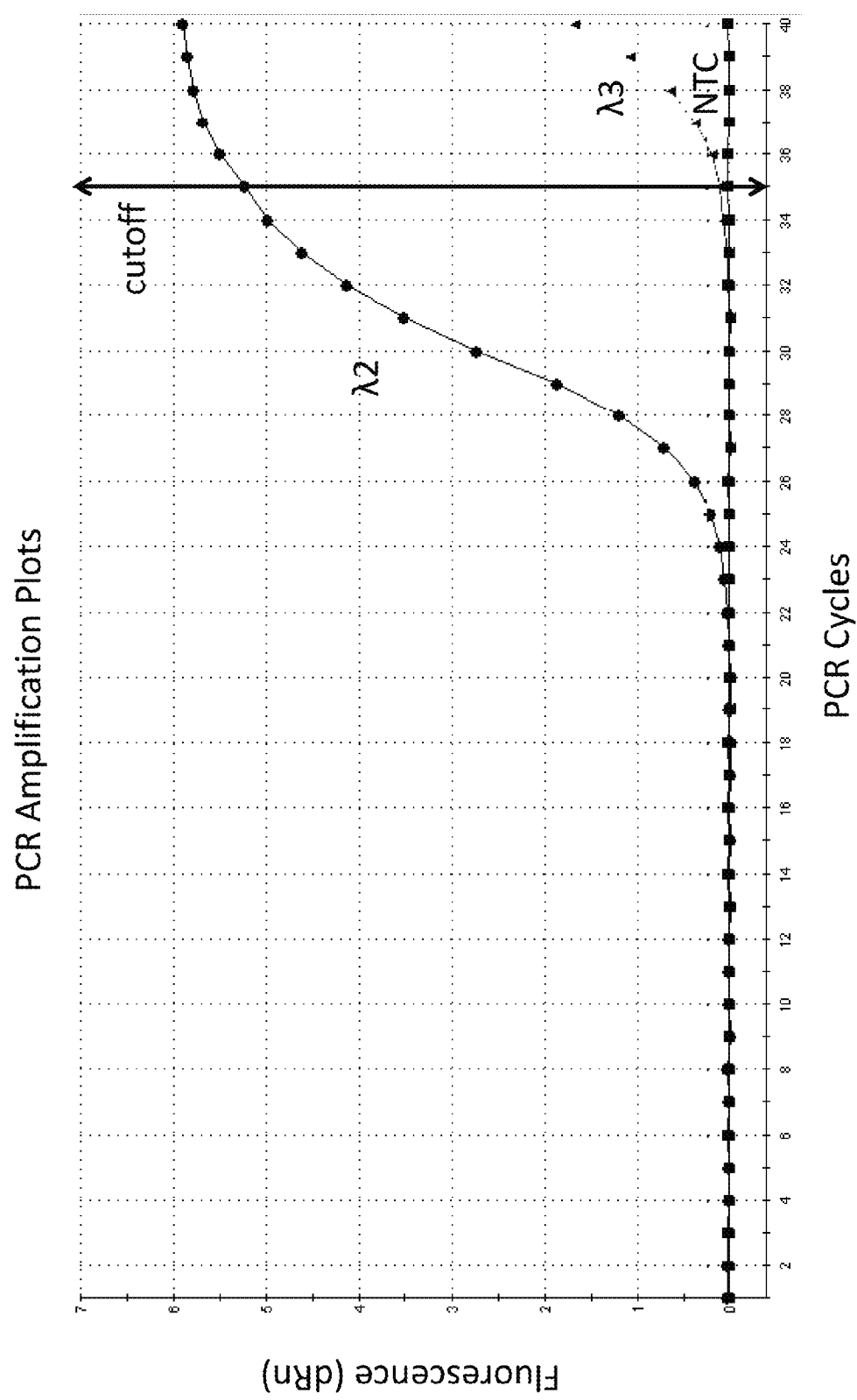
FIG. 6 depicts the specificity of the IFN-λ2 qRT-PCR. This figure shows the amplification of both IFN-λ2 (SEQ ID NO: 1) and IFN-λ3 synthetic oligos (SEQ ID NO: 2) by the IFN-λ2 primers. Note that $10^4$ copies of IFN-λ2 template is detectable at cycle 26, while amplification of the same amount of IFN-λ3 template is not detectable when the assay cutoff is set to 35 cycles and a fluorescence threshold of 0.225. These results demonstrate that the IFN-λ2 qRT-PCR is specific for IFN-λ2 does not detect IFN-λ3 under the appropriate analysis parameters (i.e., discriminates IFN-λ2 synthetic oligos from IFN-λ3 synthetic oligos). No amplification of the NTC was detected. Fluorescence is displayed as the change in the normalized reporter signal (dRn).

Using the synthesized IFN-λ3 template (i.e., SEQ ID NO: 2; detailed in Example 2), we conducted the cross-reactivity test of our selected primers (i.e., SEQ ID NOs: 3 and 4). We performed qRT-PCR assays with the selected IFN-λ2 primer pair (forward primer: SEQ ID NO: 3; reverse primer: SEQ ID NO: 4). As shown in FIG. 6, the selected IFN-λ2 primer pair successfully amplified IFN-λ2, but only negligible amplification of IFN-λ3 (at high PCR cycles), indicating very low cross-reactivity under the conditions studied (See, FIG. 6).

We next determined if the cross-reactivity may be affected by altering PCR cycles and fluorescence threshold in our qRT-PCR assay. We completely eliminated any cross-reactivity between IFN-λ2 and IFN-λ3 by optimizing the qRT-PCR. We found that by reducing the qRT-PCR cycle number to 35 and by raising the fluorescence threshold to 0.225, we were able to detect only IFN-λ2, but not IFN-λ3 (i.e., no cross-reactivity with IFN-λ3). We have established an IFN-λ2-specific qRT-PCR assay under the specified PCR condition and selected primer pair (SEQ ID NOs: 3 and 4), sufficient to detect only IFN-λ2, but not IFN-λ3. (See, Table 1).

Example 4

Amplification of IFN-λ2 From Dendritic Cells Using IFN-λ2 Specific Primers

So far, we have used chemically synthesized PCR oligo templates (i.e., SEQ ID NOS: 1 and 2) in our PCR assay. In this study, we extended our finding by employing the IFN-λ2 specific primer pair (i.e., SEQ ID NOS: 3 and 4) and confirmed the ability of our IFN-λ2 specific primers to amplify IFN-λ2 from isolated cells (e.g., dendritic cells) cDNA as opposed to the synthesized oligonucleotide templates.

Figure 7:
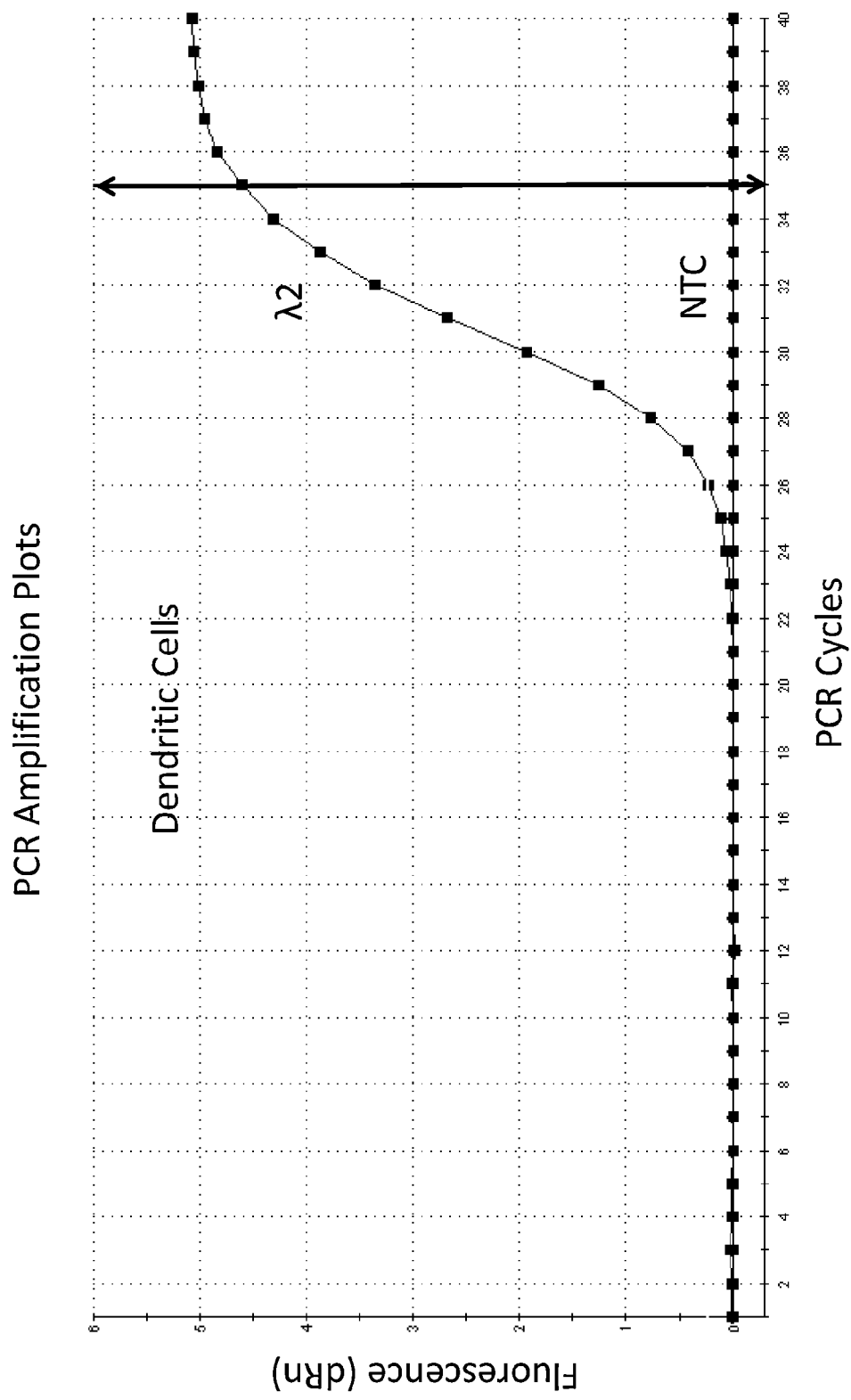
FIG. 7 depicts the detection of IFN-λ2 mRNA from virally-stimulated blood dendritic cells. Human pan-dendritic cells were isolated from peripheral blood mononuclear cells by magnetic selection. The resultant cells were cultured with HSV for 24 hours to stimulate production of IFN-λ, at which point mRNA was extracted using phenol-chloroform. cDNA was generated using reverse-transcriptase and then was examined for the presence of IFN-λ2 transcripts by qRT-PCR. The PCR amplification plot depicts the amplification of IFN-λ2 mRNA harvested from freshly-isolated, in vitro-stimulated human blood derived dendritic cells, as opposed to synthetic IFN-λ2 oligonucleotides (SEQ ID NO: 1). Fluorescence is displayed as the change in the normalized reporter signal (dRn).

We isolated human pan-dendritic cells from peripheral blood mononuclear cells by negative magnetic selection (i.e., protocol adopted from Stem Cell Technologies cat. #19251). Unwanted cells were targeted for removal by Tetrameric Antibody Complexes recognizing CD3, CD9, CD14, CD16, CD19, CD34, CD56, CD66b, glycophorin A and dextran-coated magnetic particles. The resultant dendritic cells were ~92% pure. The dendritic cells were then cultured with HSV-1 (KOS strain) at an MOI of one (1) for 24 hours to stimulate production of IFN-λ, at which point mRNA was extracted using guanidinium thiocyanate-phenol-chloroform (TRIzol®) extraction. The dendritic cell pellet was dissolved in TRIzol® and then chloroform was added. The sample was then separated into an upper aqueous layer containing the RNA and a lower, organic layer containing DNA and protein. The upper layer was extracted and washed using ethanol to obtain clean RNA.

cDNA was generated using reverse-transcriptase (in accordance with manufacturer's protocol) and examined for the presence of IFN-λ2 transcripts by qRT-PCR. The PCR amplification plot depicts the amplification of IFN-λ2 mRNA harvested from freshly-isolated, in vitro-stimulated human blood derived dendritic cells, as opposed to synthetic IFN-λ2 oligonucleotides. As shown in FIG. 7, our selected IFN-λ2 specific primers (i.e., SEQ ID NOS: 3 and 4) were successfully able to amplify IFN-λ2 from dendritic cells.

Using the dissociation curve analysis, we determined that our selected PCR primer pair (SEQ ID NOS: 3 and 4) yielded only one (1) amplicon in our qRT-PCR assay from dendritic cell cDNA, similar to that seen with the synthetic PCR template detailed in Example 3. The generation of a single peak in the dissociation curve indicates the production of one (1) single amplicon, while multiple peaks would indicate more than one amplicon.

Figure 8:
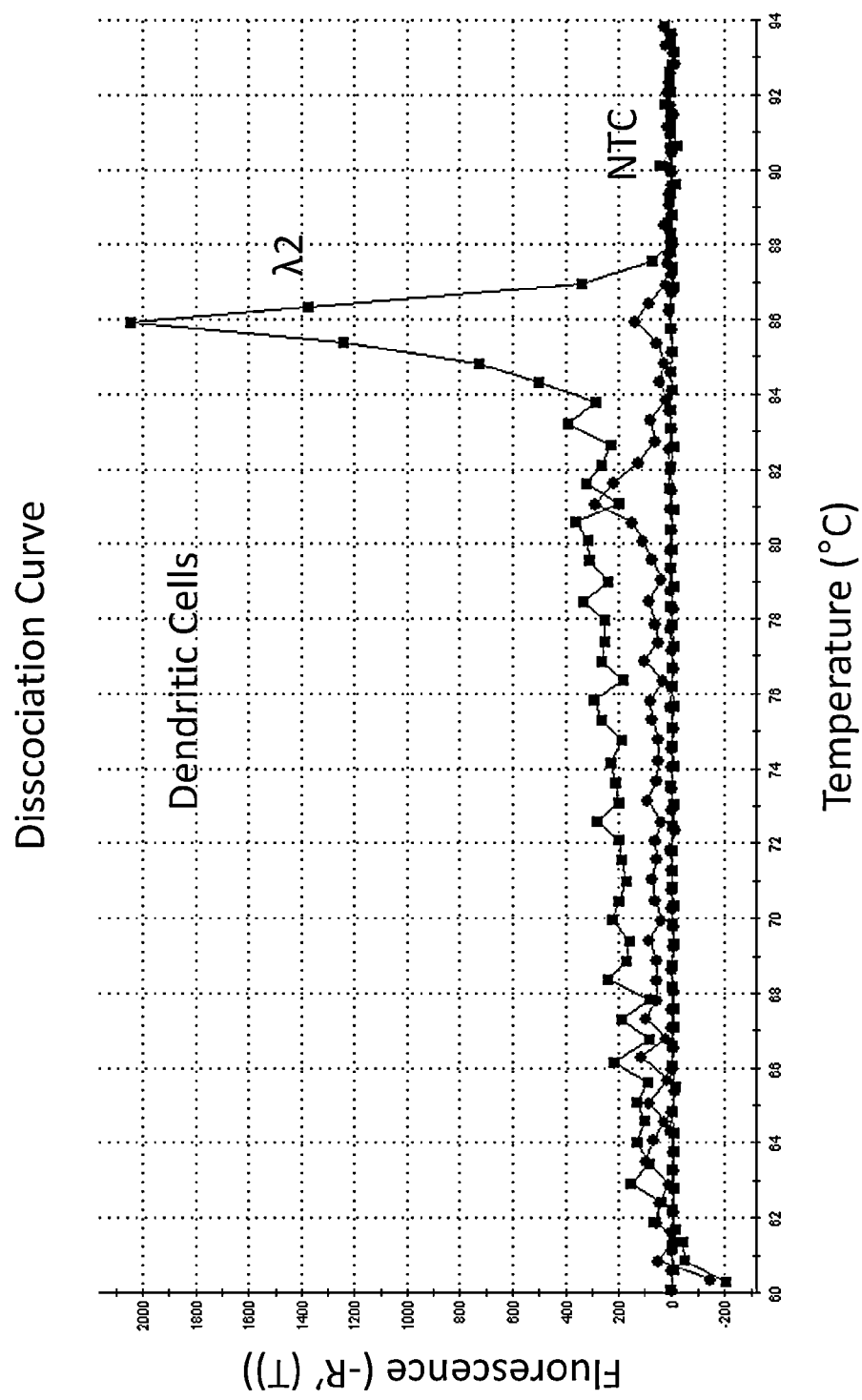
FIG. 8 depicts the dissociation curve of the amplicons generated in an IFN-λ2 qRT-PCR using dendritic cell cDNA. Note that the melting temperature of 86° C. matches that from the synthetic oligo amplicon. (See, FIG. 5). Fluorescence is shown as the negative of the decrease in fluorescence as a function of temperature (−R'(T)).

As shown in FIG. 8, we detected only one (1) single amplicon at 86° C., thus verifying the suitability of our IFN-λ2-specific primers (SEQ ID NOS: 3 and 4) used in conjunction with our qRT-PCR assay in whole cell lysates.

Example 5

Confirmation of Amplification of the Correct IFN-λ2 Amplicon in Dendritic Cells

In this example, we further conducted sequencing analysis to confirm the amplicon detected using our RT-PCR assay (in Example 5) with the selected IFN-λ2 primers (SEQ ID NOS: 3 and 4) was indeed IFN-λ2. After amplification of IFN-λ2 specific primers, the qRT-PCR product was run on an agarose gel using electrophoresis to confirm the expected size of 94 base pairs. After the size confirmation, we then proceed to excise the amplicon from the gel and isolated the DNA using a DNA-binding spin column. We then sequenced the amplicon. The nucleotide sequence of the amplicon was compared to the deposited nucleotide sequence of IFN-λ2 (accession number NM_172138.1). The sequence alignment is reported in FIG. 9 (revealing 100% identities), thus confirming that our IFN-λ2 specific primers in fact amplify IFN-λ2, and not IFN-λ3.

Example 6

Slight Modification the Primers Abolishes Amplification of IFN-λ2

FIG. 10 depicts the SEQ ID NOS: 3 and 4 and the region of IFN-λ2 that was amplified. We chose to alter the primer pairs and examined the effect on amplification of IFN-λ2.

In this study, we maintained the same forward primer (SEQ ID NO: 3), spanning base pairs 262-279 of IFN-λ2, but increased the length of the reverse primer from SEQ ID NO: 4 to 5'-GCT CAG CCT CCA AAG CCA T-3' (SEQ ID NO: 5). Note that SEQ ID NO: 4 and SEQ ID NO: 5 differed by only one (1) base pair. As detailed in FIG. 10, SEQ ID NO: 4 spans bases 338-355 whereas SEQ ID NO: 5 spans bases 338-356.

In the qRT-PCR assay, contrary to the primer pair (SEQ ID NOS: 3 and 4), we found that the primer set (composed of SEQ ID NOS: 3 and 5) did not lead to any amplification of IFN-λ2 at all.

This finding is totally unexpected and the basis for the present finding remains unknown. We found that addition of one (1) nucleotide base to the reverse primer completely ablates the utility of the primer set to amplify IFN-λ2 in our qRT-PCR assay, demonstrating a high specificity. Thus, slight modification of primer set can unexpectedly abolish its ability to amplify IFN-λ2.

Example 7

Primers Amplifying a Different Region of IFN-λ2 Fail in qRT-PCR Assay

We tested primers that lie in a different region of IFN-λ2 to test if amplification of IFN-λ2 was still possible. To that end, we prepared PCR templates for a different IFN-λ region.

PCR Templates

IFN-λ2: In order to develop a qRT-PCR assay, we continued to chemically synthesize an oligonucleotide fragment (oligo) that is identical to that of human IFN-λ2 mRNA, between 364 to 513 base pairs (See, FIG. 13). The oligo is 150 nucleotides in length (SEQ ID NO: 6). We used this prepared oligonucleotide fragment (SEQ ID NO: 6) as a PCR template to perform qRT-PCR assays.

IFN-λ3: We also chemically synthesized the oligonucleotide template for IFN-λ3. The chemical synthesized IFN-λ3 oligonucleotide fragment is 150 nucleotides in length, and has a nucleotide sequence that is identical to that of human IFN-λ3 mRNA between 304 to 453 base pairs (SEQ ID NO: 7) (See, FIG. 13).

In this second series of study, we designed a PCR forward primer between bases 397 and 415, having the sequence 5'-TGACCCAGCCCTGGTGGAC-3' (SEQ ID NO: 8) to utilize the two (2) non-homologous base pairs (i.e., T-G and C-T). We also designed a PCR reverse primer between bases 461 and 479 of sequence 5'-CTGGATACAGGCCCGGAA-3' (SEQ ID NO: 9) to utilize another non-homologous base pair (i.e., T-C) (See, FIG. 11; depicting all three sets of primers pairs tested and their location).

Using the selected PCR primer pair (SEQ ID NOS: 8 and 9), we performed a qRT-PCR assay using oligonucleotide fragment (SEQ ID NO: 6) as the PCR template. Similar to that shown in FIG. 4, we observed amplification of IFN-λ2 using these primers (SEQ ID NOS: 8 and 9). In this instance, however, we observed a strong formation of primer dimers, making this primer set (SEQ ID NOS: 8 and 9) unsuitable for quantifying IFN-λ2 expression. This is another indication that our working IFN-λ2 primers (SEQ ID NOS: 3 and 4) are unique.

Example 8 q-RT-PCR Assay Using Selected IFN-λ3-Specific Primers

We continued the following studies to examine IFN-λ3-specific primers in order to specifically detect IFN-λ3, but not IFN-λ2.

From the sequence alignment data shown in FIG. 1, we chose two (2) non-homologous nucleotide regions explore the suitability of generating IFN-λ3-specific primers.

In this third series of study, we designed a forward PCR forward primer between bases 339 and 355, having sequence 5'-ACCCAGCCCTGGGGGAT-3' (SEQ ID NO: 10), to utilize the two (2) non-homologous base pairs (i.e., G-T and T-C) (See, FIGS. 12 and 22). We also designed a reverse PCR primer between 401 and 419, having sequence 5'-GCTGGATACAGGCCCGGAG-3' (SEQ ID NO: 11), to utilize another non-homologous base pair (i.e., C-T) (See, FIGS. 12 and 22).

In this fourth series of study, we designed a forward PCR primer pair between bases 202 and 219, having a sequence 5'-GAAGGACTGCAAGTGCCA-3' (SEQ ID NO: 12) to utilize the two (2) non-homologous base pairs (i.e., A-G and G-A) (See, FIG. 22). We also designed a reverse PCR primer between bases 278 and 295 having sequence 5'-CTCAGC-CTCCAAAGCCAC-3' (SEQ ID NO: 13), to utilize another non-homologous base pair (i.e., G-A) (See, FIG. 22).

These PCR primer sets were designed specifically to examine the suitability of generating IFN-λ3 specific primers that would bind to IFN-λ3 mRNA, but not IFN-λ2.

Using the selected PCR primer pair of SEQ ID NOs: 10-11, we performed qRT-PCR assay using the oligonucleotide fragment as a PCR template (SEQ ID NO: 7). As shown in FIG. 14, we observed a dose-dependent amplification of IFN-λ3, ranging from $10^2$ to $10^5$ copies of the oligonucleotide fragment template. Note that there was no PCR signal when no oligonucleotide fragment was used as template (i.e., NTC; "no template control"). This study confirms that the designed PCR primer set is able to amplify, based on the oligonucleotide template, to produce an IFN-λ3 amplicon.

Example 9

Dissociation Curve Analysis of the qRT-PCR IFN-λ3 Amplicon

In this study, we conducted a dissociation curve analysis as described in Example 3. The generation of one (1) single peak in the dissociation curve analysis indicates the production of one (1) single amplicon, while the generation of multiple peaks reveals more than one amplicon.

As shown in FIG. 15, we detected one (1) single amplicon at 83° C., thus demonstrating that our qRT-PCR is specific to IFN-λ3 and not IFN-λ2. The dissociation curve analysis verifies the suitability of our IFN-λ3-specific primers used in conjunction with our qRT-PCR assay to distinguish between IFN-λ3 and IFN-λ2.

Example 10

Cross-Reactivity of IFN-λ3 Primers with IFN-λ2 Template

Our sequence alignment study revealed that IFN-λ3 and IFN-λ2 are highly homologous at the nucleotide level (See, Example 1, and FIG. 1). To show specificity, it is important to determine that the selected primers would amplify IFN-λ3 in our qRT-PCR assay but not IFN-λ2 (i.e., no cross-reactivity with IFN-λ2).

In this study, we used the oligonucleotide templates for both IFN-λ3 (SEQ ID NO: 7) and IFN-λ2 (SEQ ID NO: 6) respectively to conduct a cross-reactivity study of the selected primers (SEQ ID NOS: 10-11). We observed that the selected IFN-λ3 primers (i.e., SEQ ID NOS: 10-11) allowed only a minimal amplification of IFN-λ2 above PCR cycle 36, demonstrating a negligible cross-reactivity under the conditions studied (See, FIG. 16).

We next determined if cross reactivity may be affected by applying the same PCR cycle and fluorescence threshold as identified in Example 4. By applying these conditions (reducing the cycle number to thirty five (35) and fluorescence threshold to 0.225 (See, Example 4)), we successfully eliminate any cross-reactivity between the IFN-λ3 primers and the IFN-λ2 template (i.e., no cross-reactivity with IFN-λ2). We have established an IFN-λ3-specific qRT-PCR assay.

Example 11

Amplification of IFN-λ3 from Dendritic Cells Using IFN-λ3 Specific Primers

Next, we used the IFN-λ3 specific primers and tested the ability of our IFN-λ3 specific primers to amplify IFN-λ3 in whole-cell (i.e., dendritic cells) cDNA as opposed to oligonucleotide templates. Human pan-dendritic cells were isolated as previously described in Example 5.

The dendritic cells were then cultured with HSV-1 and mRNA was isolated using TRIzol® as described in Example 5. Upon isolated of mRNA, cDNA was then generated, as described in Example 5, and examined for the presence of IFN-λ3 transcripts qRT-PCR. The PCR amplification plot depicts the amplification of cDNA derived from IFN-λ3 mRNA harvested from freshly-isolated, in vitro-stimulated human blood dendritic cells, as opposed to synthetic IFN-λ3 oligonucleotides. As shown in FIG. 17, our selected IFN-λ3 specific primers were successfully able to amplify IFN-λ3 from dendritic cells.

Using the dissociation curve analysis, we further determined whether our selected PCR primer pair (See, Example 9) yield only one (1) amplicon in our qRT-PCR assay from dendritic cell cDNA, as previously seen with the synthetic template in FIG. 15. The generation of one (1) single peak in the dissociation curve indicates the production of one (1) single amplicon. Multiple peaks reveal more than one amplicon. As shown in FIG. 18, we detected only one (1) single amplicon at 83° C., thus verifying the suitability of our IFN-λ3-specific primers, used in conjunction with our qRT-PCR assay, in whole cells.

Example 12

Using the Dissociation Curve Analysis to Differentiate Between IFN-λ2 and IFN-λ3

In this example we demonstrate that IFN-λ2 and IFN-λ3 can be distinguished by their dissociation curves. As previously described in Example 3, IFN-λ2 has a melting temperature of 86° C. In Example 9 we showed that IFN-λ3 has a melting temperature of 83° C.

FIG. 19 shows an overlay of the dissociation curves for IFN-λ2 and IFN-λ3, demonstrating that the two (2) amplicons have distinct dissociation profiles and can be readily distinguished from each other.

Example 13

Confirmation of Amplification of the Correct IFN-λ3 Amplicon in Dendritic Cells

In this example, we performed sequencing analysis to confirm the amplicon detected using our qRT-PCR assay with the selected IFN-λ3 primers was indeed IFN-λ3. After amplification using IFN-λ3 specific primers, the qRT-qRT-PCR product was run on an agarose gel using electrophoresis to confirm the expected size of 81 base pairs. After the size confirmation, we then proceeded to excise the amplicon from the gel and isolated DNA using a DNA-binding spin column. We then proceeded to sequence the amplicon. The nucleotide sequence of the amplicon was compared to the deposited nucleotide sequence of IFN-λ3 (accession number NM_172139.2). The sequence alignment is reported in FIG. 20 (100% identity), confirming that our IFN-λ3 specific-primers in fact amplify IFN-λ3, and not IFN-λ2.

Example 14

Slight Modification of the Primer Set Unexpectedly Causes Non-Specific Amplification of IFN-λ2

In this experiment, we evaluated the effects of altering the nucleotide sequences of the IFN-λ3 specific primers. So far, the forward primer (SEQ ID NO: 10) and reverse primer (SEQ ID NO: 11) work as an IFN-λ3 specific primer set.

FIG. 21 depicts a modified primer set that amplifies the same region of IFN-λ3. In the modified primer set, we increased the length of the forward primer from SEQ ID NO: 10 (spanning bases 339-355 of IFN-λ3) to 5'-GAA GGA CTG CAA GTG CCA-3' (SEQ ID NO: 14) (spanning bases 337-355 of IFN-λ3), which differed by two nucleotides. We maintained the same reverse primer (i.e., SEQ ID NO: 11) that spans the base pairs 401-419 of IFN-λ3.

In the qRT-PCR assay, we discovered that the modified primer set (i.e., SEQ ID NO: 14 (forward) and SEQ ID NO: 11 (reverse) was able to amplify IFN-λ3, however they also substantially cross-reacted and amplified IFN-λ2 (therefore rendering this primer pair unsuitable). We observed that the addition of only two bases on the forward primer (SEQ ID NO: 10) ablates the utility of this primer set to be used in our qRT-PCR assay as it no longer specifically amplifies IFN-λ3.

Example 15

Primers Amplifying a Different Region of IFN-λ3 Cannot be Used in the Present qRT-PCR Assay In this experiment we tested primers that lie in a different region of IFN-λ3 to determine whether specific amplification of IFN-λ3 was still possible.

We designed a PCR forward primer between bases 202 and 219, having a sequence of 5'-GAA GGA CTG CAA GTG CCG-3' (SEQ ID NO: 12) to utilize the two (2) non-homologous base pairs (i.e., A-G and G-A) (See, FIG. 22). We also designed a PCR reverse primer between bases 278 and 295, having a sequence of 5'-CTCAGCCTC-CAAAGCCAC-3' (SEQ ID NO: 13), to utilize another non-homologous base pair (i.e., G-A) (See, FIG. 22).

Using the selected PCR primer pair (SEQ ID NO: 12 (forward) and SEQ ID NO: 13 (reverse)), we performed a qRT-PCR assay using oligonucleotide fragment (SEQ ID NO: 2) as PCR template.

Similar to that shown in FIG. 14, we observed amplification of IFN-λ3 using these primers. In this instance however, we also observed a strong amplification of IFN-λ2 (i.e., substantial cross-reactivity with IFN-λ2), making this primer set (SEQ ID NOS: 12-13) unsuitable for quantifying IFN-λ3 expression. This observation is surprising, and illustrates that our IFNλ-3 primer set (i.e., SEQ ID NO: 10 and SEQ ID NO: 11) are unique.

Example 16

Detection of IFN-λ2 and IFN-λ3 Expression Using the IFN-λ2 and IFN-λ3 Specific Primers—Differential Expression In Epithelial Cells BEAS-2B bronchial epithelial cells were cultured with the TLR3 agonist, poly IC, to mimic viral infection for up to 6 hours. Total RNA was prepared at various time points (See, FIG. 23) and converted by reverse transcription to cDNA. IFN-λ2 or IFN-λ3 mRNA transcripts were then detected by qRT-PCR using the IFN-λ2 (SEQ ID NOS. 3 and 4) or IFN-λ3 (SEQ ID NOS. 10 and 11) specific primers. IFN-λ2 and IFN-λ3 showed a similar timing in the response to poly IC stimulation; however, IFN-λ3 was induced to a higher degree. Therefore, specific detection of IFN-λ2 and IFN-λ3 allowed for the simultaneous determination that BEAS-2B cells have a more robust induction of IFN-λ3 in response to this viral mimic as compared to that of IFN-λ2 (i.e., exhibited a differential expression of IFN-λ2 and IFN-λ3 mRNA following cell stimulation in epithelial cells).

Example 17

Comparison of IFN-λ2/3 Non-Specific Primers Versus the IFN-λ2 and IFN-λ3 Specific Primers to Detect Transcript Levels in Colon Cells Stimulated with Poly IC SW480 colon adenocarcinoma cells were cultured with the TLR3 agonist, poly IC, to mimic viral infection for up to 24 hours. Total RNA was prepared at various time points and converted by reverse transcription to cDNA (See, FIG. 24). The IFN-λ2 and IFN-λ3 transcripts were detected collectively by qRT-PCR using non-specific IFN-λ2/3 primers (SEQ ID NO: 17 and SEQ ID NO: 18). Using this non-specific method of detection, the peak induction of transcripts in response to poly IC was observed at 3 hours (See, FIG. 24A). As depicted in FIG. 24B, a similar pattern was observed using specific detection of IFN-λ2 with the IFN-λ2 specific primers (SEQ ID NO: 3 and SEQ ID NO: 4). To our surprise, we failed to observe any increase IFN-λ3 transcripts in these cells using the IFN-λ3 specific primers (SEQ ID NO: 10 and SEQ ID NO: 11). These data indicate that the IFN-λ2 and IFN-λ3 specific primers can be used to detect differences in expression levels in colon cells that would be masked if these genes were detected using a single non-specific primer set.

Example 18

Comparison of IFN-λ2/3 Non-Specific Primers Versus the IFN-λ2 and IFN-λ3 Specific Primers to Detect Transcript Levels in Bronchial Epithelial Cells in Response to Manipulation of a Transcriptional Regulator BEAS-2B airway epithelial cells were transfected with siRNA directed at ZEB1, a known transcriptional repressor of IFN-λ genes (Siegel et al., 2011). 48 hours after transfection with ZEB1 or control (NT) siRNA, the cells were cultured with the TLR3 agonist poly IC to mimic viral infection for up to 4.5 hours. Total RNA was prepared at various time points and converted by reverse transcription to cDNA (FIG. 25). The IFN-λ2 and IFN-λ3 transcripts were detected collectively by qRT-PCR using non-specific IFN-λ2/3 primers (SEQ ID NO: 17 and SEQ ID NO: 18). Using this non-specific method of detection, the peak induction of transcripts in response to poly IC was observed at 3 hours and ZEB1 siRNA lead to a significant elevation of IFN-λ2/3 transcripts when compared to the control, NT siRNA (See, FIG. 25A). In contrast, there was no effect of ZEB1 siRNA on IFN-λ2 transcript levels when using the IFN-λ2 specific primers (SEQ ID NO: 3 and SEQ ID NO: 4), FIG. 25B. IFN-λ3 transcript levels were enhanced by ZEB1 siRNA as detected using the IFN-λ3 specific primers (SEQ ID NO: 10 and SEQ ID NO: 11) (See, FIG. 25C). These data indicate that the IFN-λ2 and IFN-λ3 specific primers can be used to detect differences in expression levels in bronchial epithelial cells that would be masked if these genes were detected using a single non-specific primer set.

Example 19

Comparison of IFN-λ2 and IFN-23 Specific Primers to Detect Transcript Levels in HEPG2 Hepatocellular Cells in Response to Manipulation of a Transcriptional Regulator HEPG2 hepatocellular carcinoma cells were transfected with siRNA directed at ZEB1, a known transcriptional repressor of IFN-λ genes (Siegel et al., 2011). 48 hours after transfection with ZEB1 or control (NT) siRNA the cells were infected with human Rhinovirus Type 1B and cultured for an additional 48 hours. Total RNA was prepared at various time points and converted by reverse transcription to cDNA (See, FIG. 26). The IFN-λ2 transcript levels were detected by qRT-PCR using the specific IFN-λ2 primers (SEQ ID NO: 3 and SEQ ID NO: 4). ZEB1 siRNA lead to a significant elevation of IFN-λ2 transcripts at 24 and 48 hours when compared to the control, NT siRNA (See, FIG. 26A). The IFN-λ3 transcript levels were detected by QRT-PCR using the specific IFN-λ3 primers (SEQ ID NO: 10 and SEQ ID NO: 11). ZEB1 siRNA lead to a significant elevation of IFN-λ3 transcripts at 24 and 48 hours when compared to the control, NT siRNA (See, FIG. 26A). Overall, IFN-λ3 was affected more by ZEB1 siRNA. These data indicate that the IFN-λ2 and IFN-λ3 specific primers can be used to detect differences in expression levels in liver cells that would be masked if these genes were detected using a single non-specific primer set.

Table 1 depicts a summary of the conditions tested for the IFN-λ2 assay using the synthetic oligo as template. Note that while several of these conditions produced amplification of IFN-λ2 and not IFN-λ3, not all were compatible when using cDNA isolated from cells as opposed to the synthetic oligo.

Table 2 depicts a summary of the final conditions tested on cDNA from dendritic cells. The final working conditions identified from the oligo assay (65° C. and 100 nM) were not suitable for cDNA extracted from cells. The annealing temperature of the assay was lowered to 60° C.

Table 3 depicts a summary of the conditions tested for the IFN-λ3 assay using the synthetic oligo as template. Note that while several of these conditions produced amplification of IFN-λ3 and not IFN-λ2, not all were compatible when using cDNA isolated from cells as opposed to the synthetic oligo.

Table 4 depicts a summary of the final conditions tested on cDNA from dendritic cells. The final working conditions identified from the oligo assay (65° C. and 100 nM) were not suitable for cDNA extracted from cells. The annealing temperature of the assay was lowered to 60° C.

While the present invention has been described in connection with specific embodiments thereof, it will be understood that it is capable of further modifications and this application is intended to cover any variations of the invention thereof. One of skill in the art will recognize that various modifications may be made to the embodiments described herein without departing from the spirit and scope of the invention, which is defined by the appended claims. All the references and patents cited in this application are incorporated by reference in their entirety.

What is claimed is:

1. A method of quantifying IFN-λ2 mRNA but not IFN-λ3 mRNA in a biological sample in humans, comprising the steps of:
   a) obtaining a biological sample from a human, said biological sample is suspected of having IFN-λ2 mRNA;
   b) isolating mRNA from said biological sample;
   c) performing a reverse transcription reaction to convert said mRNA to cDNA;
   d) performing a qRT-PCR on said cDNA using an IFN-λ2-specific primer set, said IFN-λ2 specific primer set containing a forward primer and a reverse primer to yield an amplification product, wherein said forward primer consists of SEQ ID NO: 3, and said reverse primer consists of SEQ ID NO: 4, wherein said IFN-λ2-specific primer set amplifies under conditions suitable for amplification of nucleic acid sequence of IFN-λ2 mRNA and not IFN-λ3 mRNA, wherein said qRT-PCR is specific for IFN-λ2 but not IFN-λ3 with low cross-reactivity as evidenced by generation of one single peak in a dissociation curve analysis; and
   e) quantifying said amplification product to determine the expression level of IFN-λ2 mRNA.

2. The method of claim 1, wherein said biological sample is a dendritic cell.

3. The method of claim 1, wherein said biological sample is an airway epithelial cell.

4. The method of claim 1, wherein said biological sample is a colon cell.

5. The method of claim 1, wherein said biological sample is a liver cell.

6. The method of claim 1, wherein said qRT-PCR step is performed using an annealing temperature of 60° C.

7. A method of quantifying IFN-λ3 mRNA but not IFN-α2 mRNA in a biological sample in humans, comprising the steps of:
   a) obtaining a biological sample from a human, said biological sample is suspected of having IFN-λ3 mRNA;
   b) isolating mRNA from said biological sample;
   c) performing a reverse transcription reaction to convert said mRNA to cDNA;
   d) performing a qRT-PCR on said cDNA using an IFN-λ3-specific primer set, said IFN-λ3 specific primer set containing a forward primer and a reverse primer, wherein said forward primer consists of SEQ ID NO: 10, and said reverse primer consists of SEQ ID NO: 11 to yield an amplification product, wherein said IFN-λ3-specific primer set amplifies under conditions suitable for amplification of nucleic acid sequence of IFN-λ3 mRNA and not IFN-λ2 mRNA, wherein said qRT-PCR is specific for IFN-λ3 but not IFN-λ2 low cross-reactivity as evidenced by generation of one single peak in a dissociation curve analysis; and
   e) quantifying said amplification product to determine the expression level of the IFN-λ3 mRNA.

8. The method of claim 7, wherein said biological sample is a dendritic cell.

9. The method of claim 7, wherein said biological sample is an airway epithelial cell.

10. The method of claim 7, wherein said biological sample is a colon cell.

11. The method of claim 7, wherein said biological sample is a liver cell.

12. The method of claim 1, wherein said qRT-PCR step is performed using an annealing temperature of 60° C.

* * * * *